United States Patent
Ball et al.

(10) Patent No.: US 10,731,209 B2
(45) Date of Patent: Aug. 4, 2020

(54) LOADING MOLECULES INTO SAMPLE WELLS FOR ANALYSIS

(71) Applicant: Quantum-Si Incorporated, Guilford, CT (US)

(72) Inventors: James A. Ball, Ledyard, CT (US); Jeremy Lackey, Guilford, CT (US); Brian Reed, Madison, CT (US); Alexander Goryaynov, New Haven, CT (US); Jonathan M. Rothberg, Guilford, CT (US); Thomas Christian, Killingworth, CT (US)

(73) Assignee: Quantum-Si Incorporated, Guilford, CT (US)

( * ) Notice: Subject to any disclaimer, the term of this patent is extended or adjusted under 35 U.S.C. 154(b) by 0 days.

(21) Appl. No.: 15/847,001

(22) Filed: Dec. 19, 2017

(65) Prior Publication Data

US 2018/0223353 A1 Aug. 9, 2018

Related U.S. Application Data

(60) Provisional application No. 62/436,407, filed on Dec. 19, 2016.

(51) Int. Cl.
| | |
|---|---|
| *C12Q 1/6869* | (2018.01) |
| *C12Q 1/6806* | (2018.01) |
| *B01L 3/00* | (2006.01) |
| *B01L 9/00* | (2006.01) |
| *C08L 1/02* | (2006.01) |
| *C08L 71/08* | (2006.01) |

(52) U.S. Cl.
CPC ........ *C12Q 1/6869* (2013.01); *B01L 3/50857* (2013.01); *B01L 9/523* (2013.01); *C08L 1/02* (2013.01); *C08L 71/08* (2013.01); *C12Q 1/6806* (2013.01); *B01L 2200/0642* (2013.01); *B01L 2300/0829* (2013.01); *B01L 2300/0893* (2013.01); *C08L 2203/16* (2013.01)

(58) Field of Classification Search
CPC ........ C12Q 1/6869; C08L 71/08; B01L 9/523
See application file for complete search history.

(56) References Cited

U.S. PATENT DOCUMENTS

| | | | |
|---|---|---|---|
| 6,264,825 B1 * | 7/2001 | Blackburn | B82Y 15/00 205/777.5 |
| 6,429,258 B1 | 8/2002 | Morgan et al. | |
| 6,517,776 B1 * | 2/2003 | Rodgers | B65B 55/08 118/317 |
| 7,399,590 B2 * | 7/2008 | Piepenburg | C12Q 1/6844 435/6.14 |
| 9,606,058 B2 | 3/2017 | Rothberg et al. | |
| 9,617,594 B2 | 4/2017 | Rothberg et al. | |
| 9,678,012 B2 | 6/2017 | Rothberg et al. | |
| 9,696,258 B2 | 7/2017 | Rothberg et al. | |
| 9,759,658 B2 | 9/2017 | Rothberg et al. | |
| 9,784,679 B2 | 10/2017 | Rothberg et al. | |
| 9,863,880 B2 | 1/2018 | Rothberg et al. | |
| 9,921,157 B2 | 3/2018 | Rothberg et al. | |
| 9,983,135 B2 | 5/2018 | Rothberg et al. | |
| 10,048,208 B2 | 8/2018 | Rothberg et al. | |
| 10,174,363 B2 | 1/2019 | Rothberg et al. | |
| 2006/0234901 A1 | 10/2006 | Scheuing et al. | |
| 2008/0032301 A1 | 2/2008 | Rank et al. | |
| 2013/0296195 A1 | 11/2013 | Gray et al. | |
| 2015/0141267 A1 | 5/2015 | Rothberg et al. | |
| 2015/0141268 A1 | 5/2015 | Rothberg et al. | |
| 2015/0177150 A1 | 6/2015 | Rothberg et al. | |
| 2016/0041095 A1 | 2/2016 | Rothberg et al. | |
| 2016/0133668 A1 | 5/2016 | Rothberg et al. | |
| 2016/0341664 A1 | 11/2016 | Rothberg et al. | |
| 2016/0344156 A1 | 11/2016 | Rothberg et al. | |
| 2016/0369332 A1 | 12/2016 | Rothberg et al. | |
| 2016/0370291 A1 | 12/2016 | Rothberg et al. | |
| 2016/0370292 A1 | 12/2016 | Rothberg et al. | |
| 2016/0377543 A1 | 12/2016 | Rothberg et al. | |
| 2016/0380025 A1 | 12/2016 | Rothberg et al. | |
| 2017/0107562 A1 | 4/2017 | Rothberg et al. | |
| 2017/0136433 A1 * | 5/2017 | Sun | B01J 19/0046 |
| 2017/0349944 A1 | 12/2017 | Rothberg et al. | |
| 2017/0350818 A1 | 12/2017 | Rothberg et al. | |
| 2017/0362651 A1 | 12/2017 | Rothberg et al. | |
| 2018/0208911 A1 | 7/2018 | Reed et al. | |
| 2018/0326412 A1 | 11/2018 | Rothberg et al. | |

FOREIGN PATENT DOCUMENTS

| | | |
|---|---|---|
| EP | 0 702 090 A2 | 3/1996 |
| EP | 2 743 535 A1 | 6/2014 |
| WO | WO 1996/21036 A2 | 7/1996 |
| WO | WO 2013/158982 A1 | 10/2013 |
| WO | WO 2015038954 * | 3/2015 |

OTHER PUBLICATIONS

Bloomfield, DNA condensation, 1996, Current Opinion in Structural Biology, 6:334-341 (Year: 1996).*
Sasaki et al, Molecular crowding improves bead-based padlock rolling circle amplification, 2017, Analytical Biochemistry, 519, 15-18. Publicly avaialable on Dec. 7, 2016. (Year: 2016).*
International Search Report and Written Opinion for International Application No. PCT/US2018/031125 dated Jul. 9, 2018.
International Search Report and Written Opinion for International Application No. PCT/US2017/067421 dated Mar. 6, 2018.
International Preliminary Report on Patentability for International Application No. PCT/US2017/067421 dated Jul. 4, 2019.
Aumiller et al., Interactions of macromolecular crowding agents and cosolutes with small-molecule substrates: effect on horseradish peroxidase activity with two different substrates. J Phys Chem B. Sep. 11, 2014;118(36):10624-32. doi: 10.1021/jp506594f. Epub Aug. 26, 2014.

(Continued)

*Primary Examiner* — Narayan K Bhat
(74) *Attorney, Agent, or Firm* — Wolf, Greenfield & Sacks, P.C.

(57) ABSTRACT

Methods of loading a molecule of interest into a sample well are provided. In some aspects, methods of loading a molecule of interest into a sample well involve loading a molecule of interest into a sample well in the presence of a crowding agent and/or a condensing agent. In some aspects, methods of loading a sequencing template into a sample well are provided.

19 Claims, 11 Drawing Sheets

(56) References Cited

OTHER PUBLICATIONS

Ballantyne et al., Molecular crowding increases the amplification success of multiple displacement amplification and short tandem repeat genotyping. Anal Biochem. Aug. 15, 2006;355(2):298-303. Epub May 11, 2006.
Bhat et al., Steric exclusion is the principal source of the preferential hydration of proteins in the presence of polyethylene glycols. Protein Sci. Sep. 1992;1(9):1133-43.
Christiansen et al., Effects of macromolecular crowding agents on protein folding in vitro and in silico. Biophys Rev. Jun. 2013;5(2):137-145. doi: 10.1007/s12551-013-0108-0. Epub Feb. 19, 2013.
Heller, DNA Microarray Technology: Devices, Systems and Applications. Annu Rev Biomed Eng. 2002;4:129-53. Epub Mar. 22, 2002.
Kuznetsova et al., What macromolecular crowding can do to a protein. Int J Mol Sci. Dec. 12, 2014;15(12):23090-140. doi: 10.3390/ijms151223090.
Nwe et al., Growing applications of "click chemistry" for bioconjugation in contemporary biomedical research. Cancer Biother Radiopharm. Jun. 2009;24(3):289-302. doi: 10.1089/cbr.2008.0626.
Phillip et al., Common crowding agents have only a small effect on protein-protein interactions. Biophys J. Aug. 5, 2009;97(3):875-85. doi: 10.1016/j.bpj.2009.05.026.
Tokuriki et al., Protein folding by the effects of macromolecular crowding. Protein Sci. Jan. 2004;13(1):125-33.
Tuske et al., The J-helix of *Escherichia coli* DNA polymerase I (Klenow fragment) regulates polymerase and 3'-5'-exonuclease functions. J Biol Chem. Aug. 4, 2000;275(31):23759-68.
Zimmerman et al., Macromolecular crowding increases binding of DNA polymerase to DNA: An adaptive effect. Proceedings of National Academy of Sciences. 1987;84(7):1871-5.

\* cited by examiner

LOADING MOLECULES INTO SAMPLE WELLS FOR ANALYSIS

RELATED APPLICATIONS

This application claims priority under 35 U.S.C. § 119(e) to U.S. Provisional Patent Application No. 62/436,407, filed Dec. 19, 2016, which is hereby incorporated by reference in its entirety.

FIELD OF THE APPLICATION

The present application is directed generally to methods and compositions for the preparation of biological and/or chemical samples for analysis.

BACKGROUND

Advancements in next-generation sequencing technologies have made it possible to conduct massively parallel analysis of single molecules. These techniques have fundamentally altered the landscape of life science research, particularly with respect to genomics and medical diagnosis. The inherent complexity of biological samples generally necessitates laborious and time consuming sample preparation protocols using conventional single molecule technologies. Moreover, the exceptionally small size of the sample wells in which these reactions are performed can be restrictive of the size of molecules capable of being analyzed.

SUMMARY

Aspects of the technology disclosed herein relate to methods of preparing molecules of interest for analysis. In some embodiments, methods and compositions useful in the preparation of samples (e.g., nucleic acid samples) for sequencing analysis are provided herein. In some embodiments, techniques described herein are related to methods of loading a sample comprising a molecule of interest into a sample well. In some aspects, the disclosure provides methods of loading a sample comprising a molecule of interest into a sample well that involve contacting the sample to a surface of a substrate. In some embodiments, the molecule of interest comprises a sequencing template. In some embodiments, a sequencing template comprises a nucleic acid molecule having at least one hybridized primer/polymerizing enzyme complex. In some embodiments, the substrate is an integrated device. In some embodiments, the surface of the substrate comprises a plurality of sample wells. In some embodiments, the methods further involve contacting the sample with a crowding agent. In some embodiments, the crowding agent excludes the molecule of interest. In some embodiments, the crowding agent selectively excludes the molecule of interest (e.g., a sequencing template) relative to solvent molecules (e.g., water) and/or other reaction components (e.g., salt, buffer, nucleotides, etc.). In some embodiments, the crowding agent is a volume excluding agent.

In some embodiments, the crowding agent is a polysaccharide. In some embodiments, the polysaccharide is a cellulose compound. In some embodiments, the cellulose compound is methyl cellulose. In some embodiments, the cellulose compound is selected from ethyl cellulose, ethyl methyl cellulose, hydroxyethyl cellulose, hydroxypropyl cellulose, hydroxyethyl methyl cellulose, hydroxypropyl methyl cellulose, ethyl hydroxyethyl cellulose, and carboxymethyl cellulose. In some embodiments, the crowding agent is a polyether compound. In some embodiments, the polyether compound is selected from polyethylene glycol, polypropylene glycol, paraformaldehyde, polytetramethylene glycol, and polyphenyl ether. In some embodiments, the crowing agent is a polyamide. In some embodiments, the polyamide is selected from linear polyvinylpyrrolidone and cyclic polyvinylpyrrolidone.

In some embodiments, the crowding agent is provided as a film. In some embodiments, the film is a material selected from a crosslinked gel or a dehydrated solution. In some embodiments, the film comprises polyacrylamide, dextran, agarose, or some combination or variant thereof. In some embodiments, the film is provided as a slurry. In some embodiments, the film is provided as particles.

In some embodiments, the crowding agent (e.g., methyl cellulose) is provided as a solution. In some embodiments, the concentration of the crowding agent in the solution is about 2.0% by weight. In some embodiments, the concentration of the crowding agent in the solution is about 2.3% by weight. In some embodiments, the concentration of the crowding agent in the solution is between about 0.1% by weight to about 1.0% by weight, between about 1.0% by weight to about 2.0% by weight, between about 2.0% by weight to about 3.0% by weight, between about 3.0% by weight to about 4.0% by weight, or between about 4.0% by weight to about 5.0% by weight. In some embodiments, the concentration of the crowding agent in the solution is between about 5.0% by weight to about 6.0% by weight, between about 6.0% by weight to about 7.0% by weight, between about 7.0% by weight to about 8.0% by weight, between about 8.0% by weight to about 9.0% by weight, or between about 9.0% by weight to about 10% by weight. In some embodiments, the concentration of the crowding agent in the solution is between about 10% by weight to about 11% by weight, between about 11% by weight to about 12% by weight, between about 12% by weight to about 13% by weight, between about 13% by weight to about 14% by weight, or between about 14% by weight to about 15% by weight.

In some embodiments, the solubility of a crowding agent depends on temperature, pH, salt, and/or other factors. In some embodiments, a crowding agent is provided in a suspension (e.g., a colloidal suspension). In some embodiments, the concentration of the crowding agent in the suspension is at about any one of the % by weights or weight ranges described above for crowding agent solutions.

In some embodiments, the sample is contacted to the surface prior to being contacted with the crowding agent. In some embodiments, the sample is contacted with the crowding agent prior to being contacted to the surface. In some embodiments, the sample is contacted to the surface and contacted with the crowding agent at approximately the same time. In some embodiments, the sample is contacted with the crowding agent upon being contacted to the surface.

In some embodiments, a sample comprising a molecule of interest is contacted to a surface of an integrated device (e.g., a sequencing chip comprising a plurality of sample wells), and a layer of crowding agent (e.g., of a solution comprising a crowding agent) is applied at the upper surface of the sample.

In some embodiments, a first solution comprising a molecule of interest is contacted to a surface of an integrated device to form a first volume at the surface of the integrated device. In some embodiments, a second solution comprising a crowding agent is contacted to a surface of the first volume to form a second volume at the surface of the first volume. In some embodiments, the crowding agent preferentially excludes the molecule of interest from the second volume relative to solvent molecules of the first volume. In some embodiments, the first solution comprises one or more reagent components (e.g., buffer, salt, labeled nucleotides). In some embodiments, the crowding agent preferentially excludes the molecule of interest from the second volume relative to the one or more reagent components of the first volume.

In some embodiments, each of the plurality of sample wells comprises a bottom surface distal to the surface of the substrate. In some embodiments, the bottom surface comprises a coupling group configured to bind the molecule of interest. In some embodiments, the bottom surface comprises a coupling group configured to bind a sequencing template (e.g., via coupling to a polymerizing enzyme or to a nucleic acid bound by a polymerizing enzyme on the sequencing template). In some embodiments, the crowding agent directs the molecule of interest toward the bottom surface, whereby the molecule of interest becomes bound to the bottom surface through the at least one coupling group. In some embodiments, the coupling group is selected from biotin, avidin, streptavidin, neutravidin, a lectin protein, or a SNAP-tag. In some embodiments, the coupling group is a reactive chemical group. In some embodiments, the reactive chemical group is selected from an amine group, an azido group, a carboxyl group, a hydroxyl group, an alkyl group, or a sulfhydryl group.

In some embodiments, a sample comprises a nucleic acid template, a polymerizing enzyme, a primer that is complementary to the nucleic acid template, and one or more reagent components suitable for a sequencing reaction. In some embodiments, the polymerizing enzyme and the primer form at least one hybridized complex on the nucleic acid template. In some embodiments, the sample further comprises one or more nucleotides (e.g., labeled nucleotides), one or more buffering agents, one or more salts, one or more reducing agents, and one or more surfactants. In some embodiments, the sample further comprises a metal cation (e.g., magnesium ion). In some embodiments, the metal cation is added to the sample to initiate a sequencing reaction.

In some embodiments, the nucleic acid molecule is between about 1 kb to about 5 kb, between about 5 kb to about 10 kb, between about 10 kb to about 15 kb, between about 15 kb to about 20 kb, or between about 20 kb to about 25 kb. In some embodiments, the nucleic acid molecule is between about 25 kb to about 50 kb, between about 50 kb to about 100 kb, between about 100 kb to about 250 kb, between about 250 kb to about 500 kb, or between about 500 kb to about 1000 kb.

In some embodiments, the polymerizing enzyme is a DNA polymerase. In some embodiments, the DNA polymerase is a T4 DNA polymerase. In some embodiments, the DNA polymerase is a T7 DNA polymerase. In some embodiments, the DNA polymerase is a phi29 DNA polymerase. In some embodiments, the DNA polymerase is an M2Y DNA polymerase. In some embodiments, the DNA polymerase is a DNA polymerase of *Lucilia cuprina*. In some embodiments, the polymerizing agent is a chimeric and/or modified DNA polymerase.

In some embodiments, a condensing agent is contacted to a molecule of interest (e.g., a sequencing template). In some embodiments, the condensing agent is contacted to the molecule of interest prior to the addition of a crowding agent. In some embodiments, the condensing agent is added to the sequencing template prior to the sequencing template being contacted to a surface of an integrated device. In some embodiments, the condensing agent and the sequencing agent are contacted to the surface of the integrated device at approximately the same time. In some embodiments, the surface of the integrated device comprises the condensing agent prior to the sequencing template being contacted to the surface of the integrated device.

In some embodiments, methods provided herein further comprise contacting the sample with a sealant. In some embodiments, the sealant comprises a mineral oil. In some embodiments, the sealant comprises an oxygen scavenging sealant that comprises an oxidizable agent and a catalyst. In some embodiments, the oxidizable agent is an organic compound comprising at least one ethylenic bond. In some embodiments, the organic compound comprises an ascorbyl group. In some embodiments, the organic compound is an ascorbyl acid ester. In some embodiments, the organic compound is a fatty acid ester of ascorbate. In some embodiments, the organic compound is a tocopherol compound. In some embodiments, the catalyst comprises a transition metal and a counterion. In some embodiments, the transition metal is selected from scandium, titanium, vanadium, chromium, manganese, iron, cobalt, nickel, copper, zinc, lanthanum, cerium, praseodymium, neodymium, promethium, samarium, europium, gadolinium, terbium, dysprosium, holmium, erbium, thulium, ytterbium, and lutetium. In some embodiments, the transition metal is copper. In some embodiments, the counterion is selected from halide (e.g., F, Cl, Br, I), sulfate, sulfite, sulfide, nitrate, nitrite, acetate, acetylacetonate, perchlorate, hydroxide, methoxide, and ethoxide. In some embodiments, the counterion is selected from laurate, myristate, palmitate, stearate, oleate, and linoleate.

In some embodiments, methods provided herein further comprise subjecting the molecule of interest (e.g., sequencing template) to a next generation sequencing technique.

BRIEF DESCRIPTION OF THE DRAWINGS

The skilled artisan will understand that the figures, described herein, are for illustration purposes only. It is to be understood that, in some instances, various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

The features and advantages of the present invention will become more apparent from the detailed description set forth below when taken in conjunction with the drawings.

When describing embodiments in reference to the drawings, direction references ("above," "below," "top," "bottom," "left," "right," "horizontal," "vertical," etc.) may be used. Such references are intended merely as an aid to the reader viewing the drawings in a normal orientation. These directional references are not intended to describe a preferred or only orientation of an embodied device. A device may be embodied in other orientations.

As is apparent from the detailed description, the examples depicted in the figures (e.g., FIGS. 1-10) and further described for the purpose of illustration throughout the application describe non-limiting embodiments, and in some cases may simplify certain processes or omit features or steps for the purpose of clearer illustration.

Figure 1:
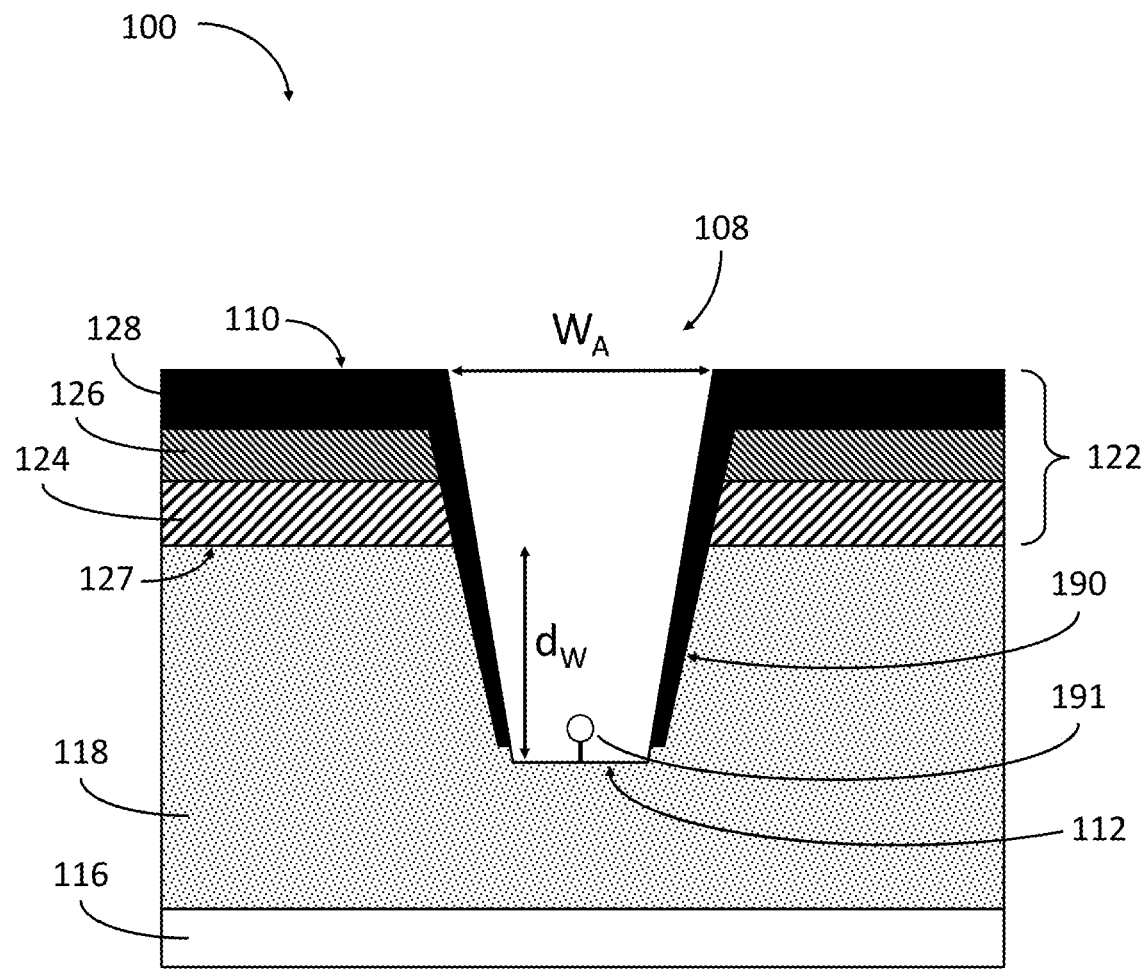

FIG. 1 is a cross-sectional view illustrating a sample well.

Figure 2:
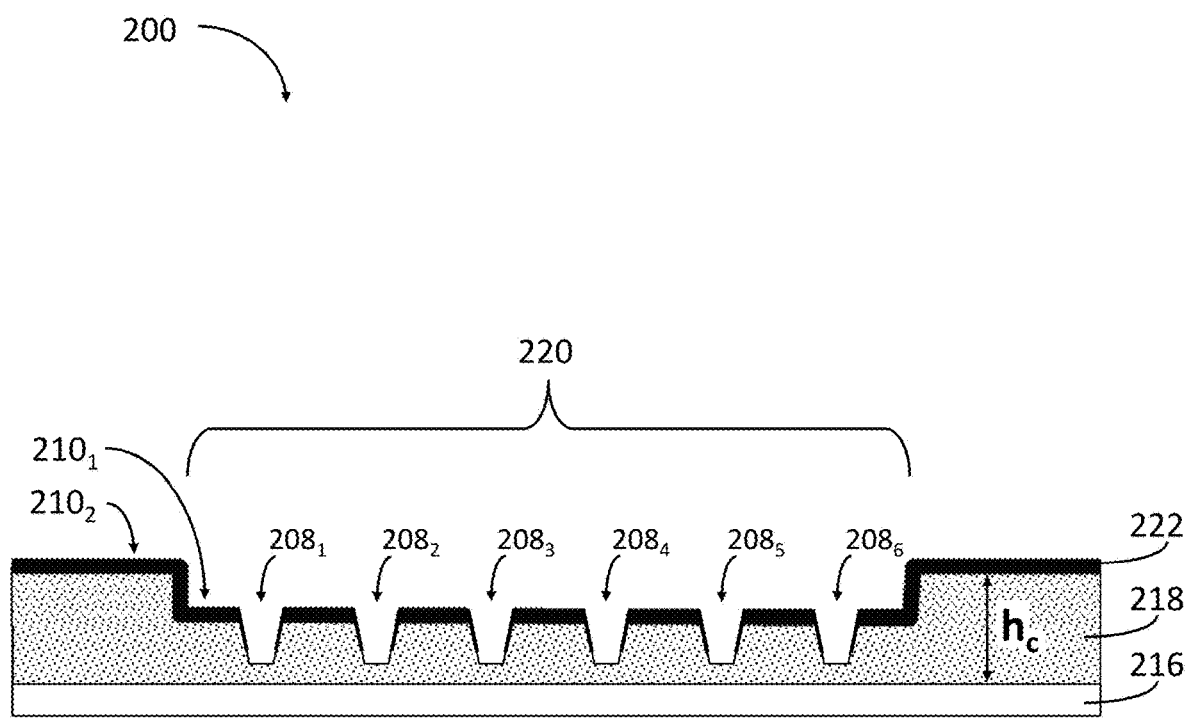

FIG. 2 is a cross-sectional view of an integrated device having a plurality of sample wells.

Figure 3A:
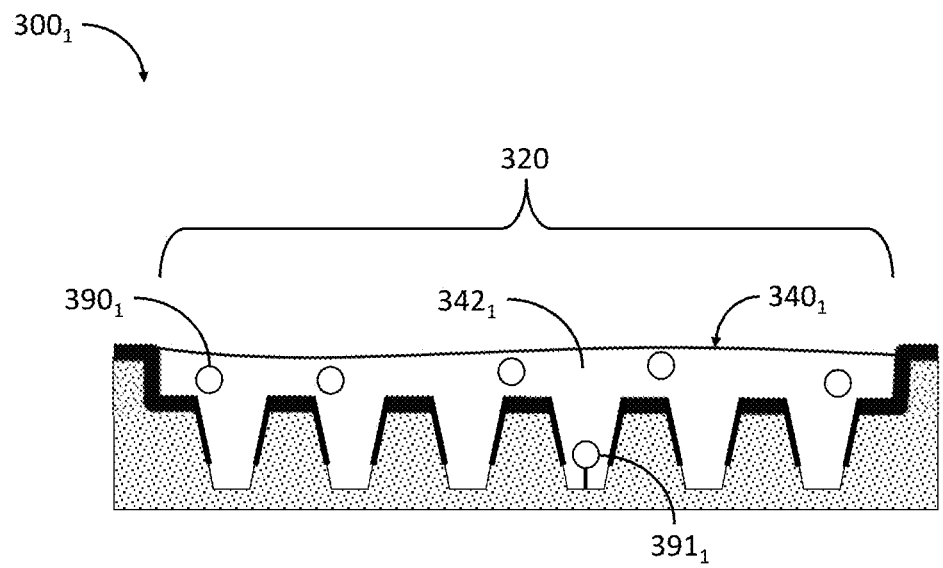

FIG. 3A is a cross-sectional view illustrating a sample comprising a molecule of interest loaded into sample wells following introduction of the sample onto an integrated device having a plurality of sample wells in the absence of crowding agent.

Figure 3B:
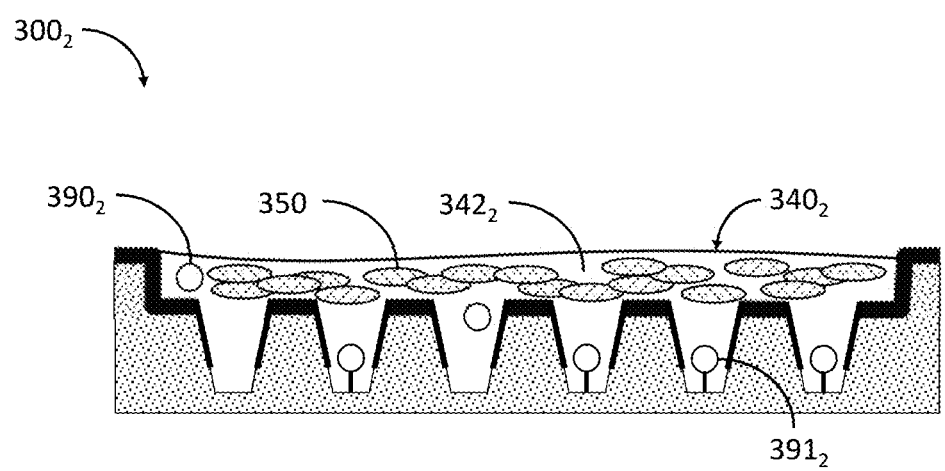

FIG. 3B is a cross-sectional view illustrating a sample comprising a molecule of interest loaded into sample wells following introduction of the sample onto an integrated device having a plurality of sample wells in the presence of crowding agent.

Figure 4:
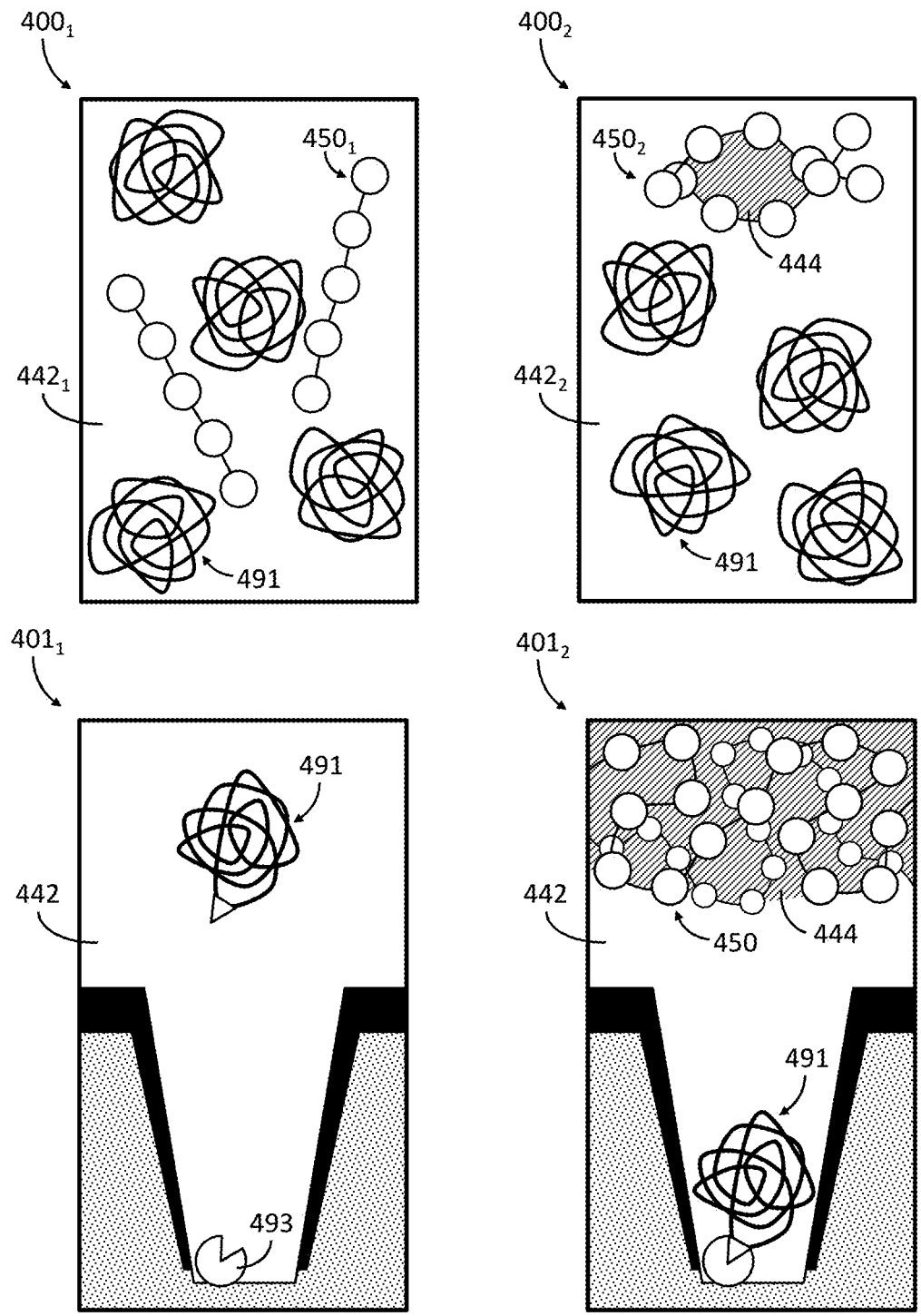

FIG. 4 is an illustration depicting an example of the effects of a crowding agent in a sample with a molecule of interest.

Figure 5:
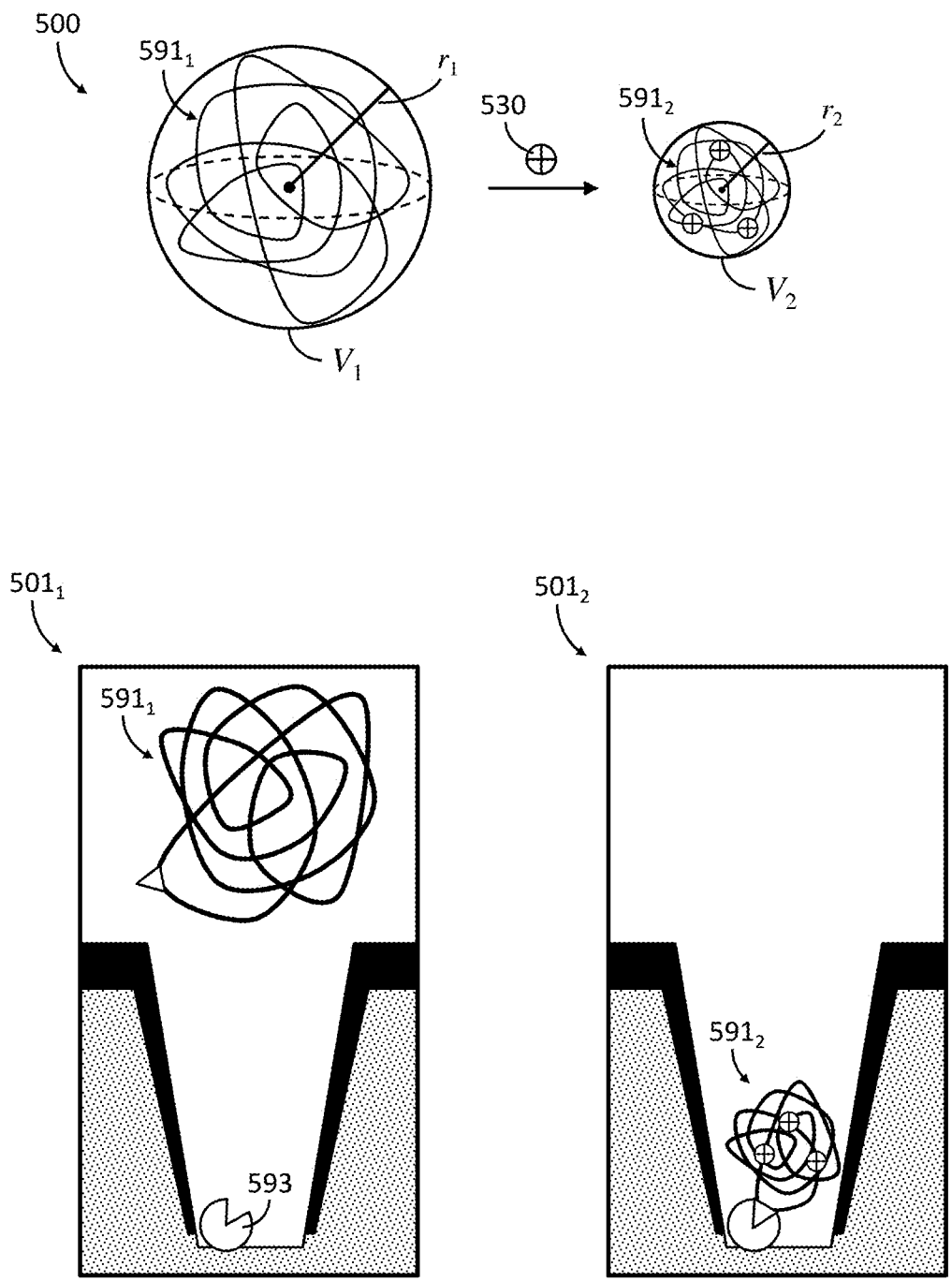

FIG. 5 is an illustration depicting an example of the effects of a condensing agent in a sample with a molecule of interest.

Figure 6A:
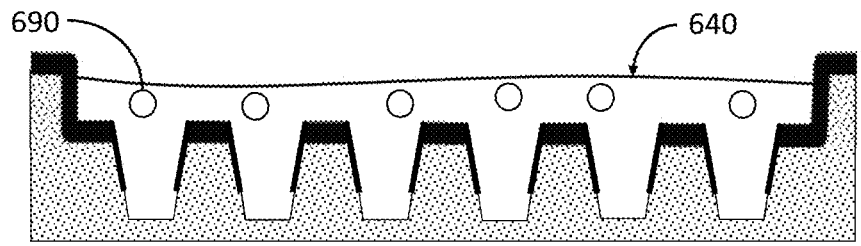
Figure 6B:
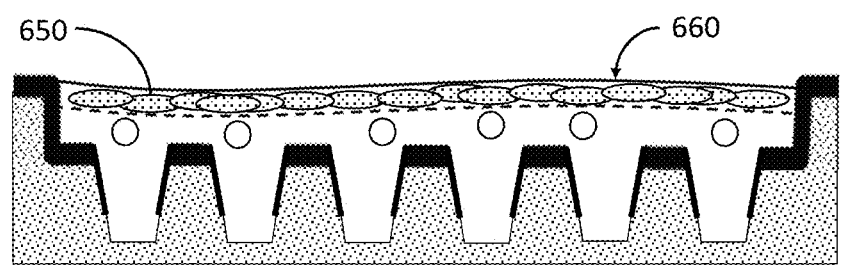
Figure 6C:
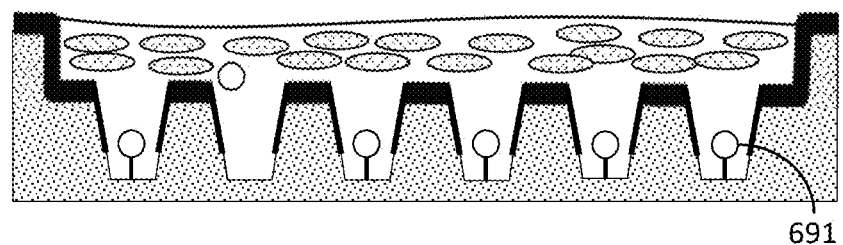

FIGS. 6A-6C depict a process whereby a sample that comprises a molecule of interest is loaded into sample wells by introducing the sample onto an integrated device (FIG. 6A), adding a crowding agent to the sample (FIG. 6B), and allowing the crowding agent to drive the molecules of interest into sample wells of the integrated device (FIG. 6C).

Figure 6D:
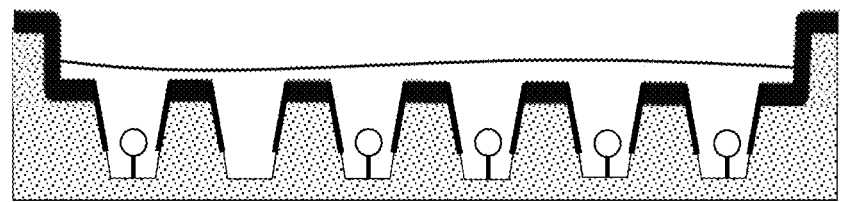

FIG. 6D is a cross-sectional view illustrating molecules of interest loaded into sample wells of an integrated device following removal of excess volume comprising the crowding agent.

Figure 6E:
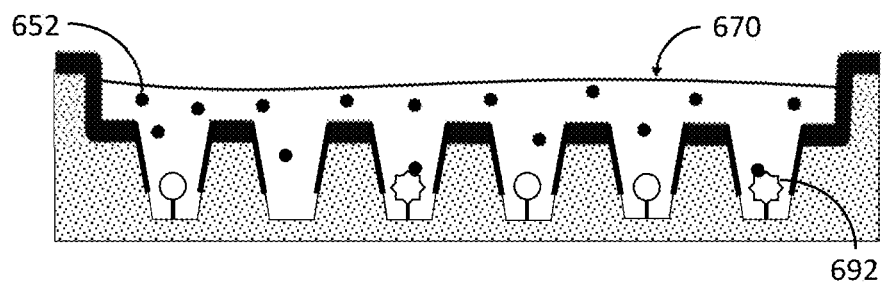

FIG. 6E depicts the integrated device of FIG. 6D following initiation of a reaction.

Figure 6F:
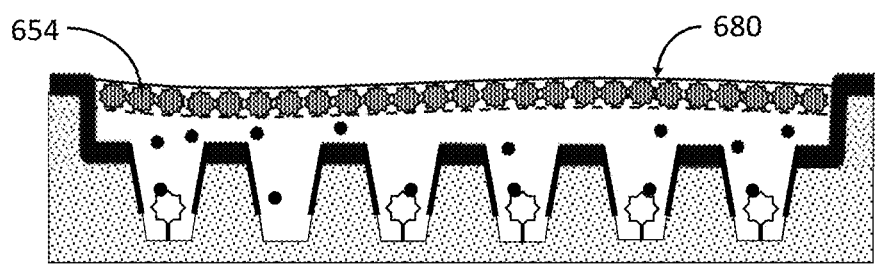

FIG. 6F depicts the integrated device of FIG. 6E following the addition of an oxygen scavenging sealant.

Figures 7A, 7B:
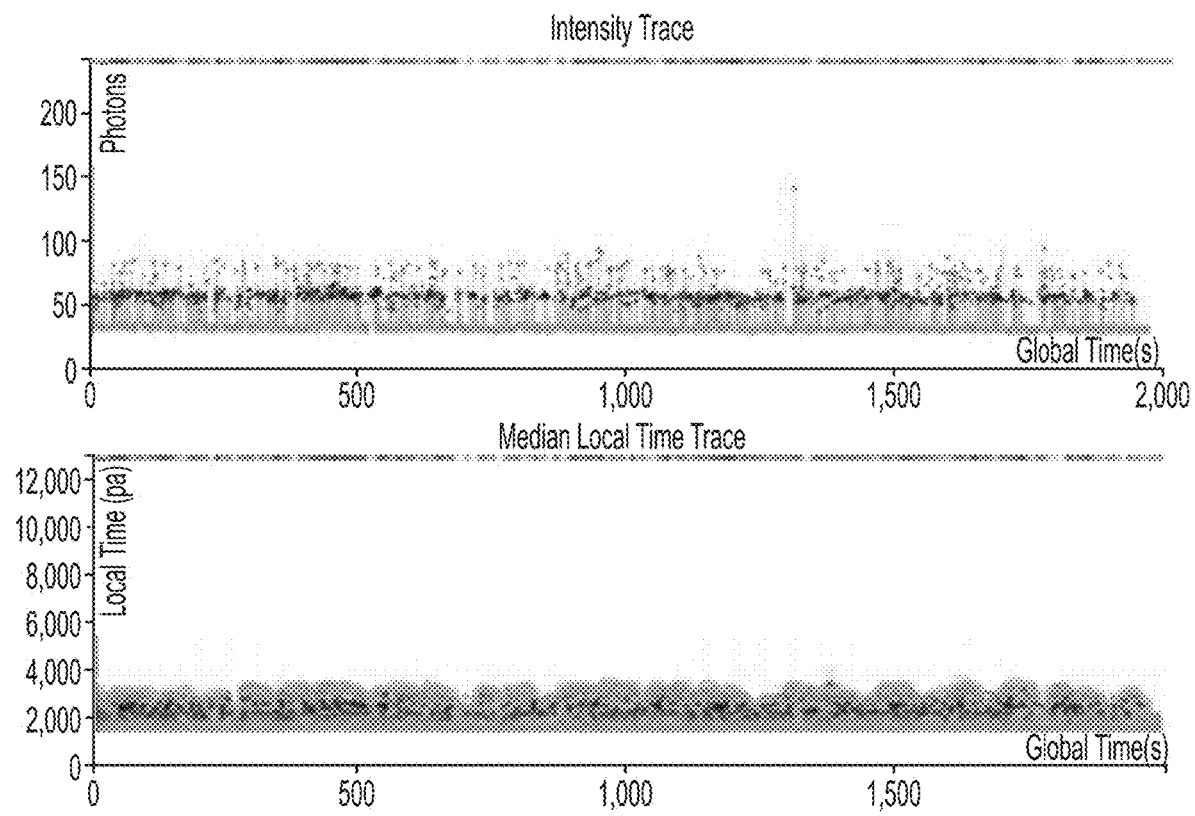

FIGS. 7A and 7B depict a readout (FIG. 7A) and results (FIG. 7B) from a real-time sequencing reaction performed using a sample that had been loaded using a crowding agent.

Figure 8:
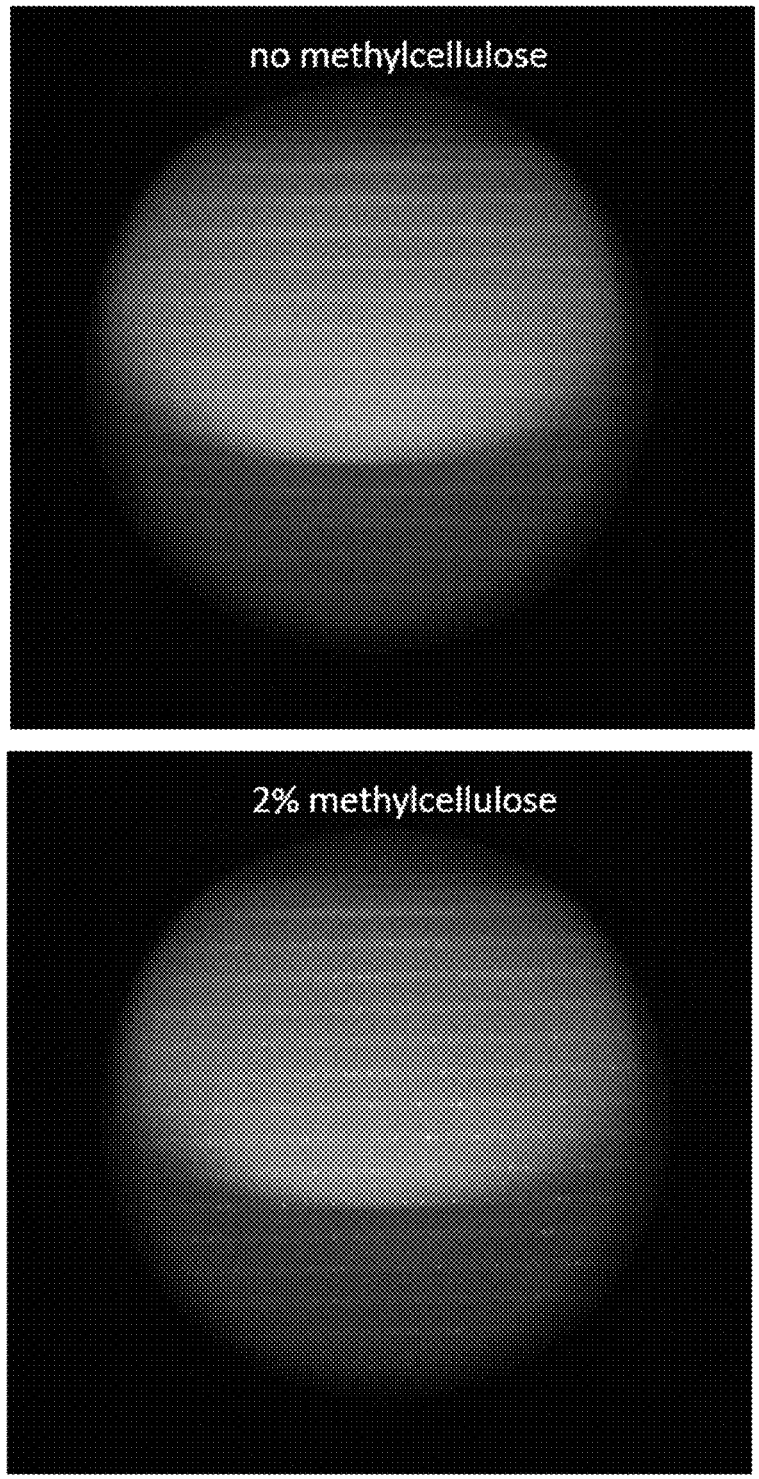

FIG. 8 depicts image representations of DNA fluorescence staining of a nucleic acid sample loaded into a sample well by diffusion (top) and a nucleic acid sample loaded into a sample well in the presence of a crowding agent (bottom).

Figure 9:
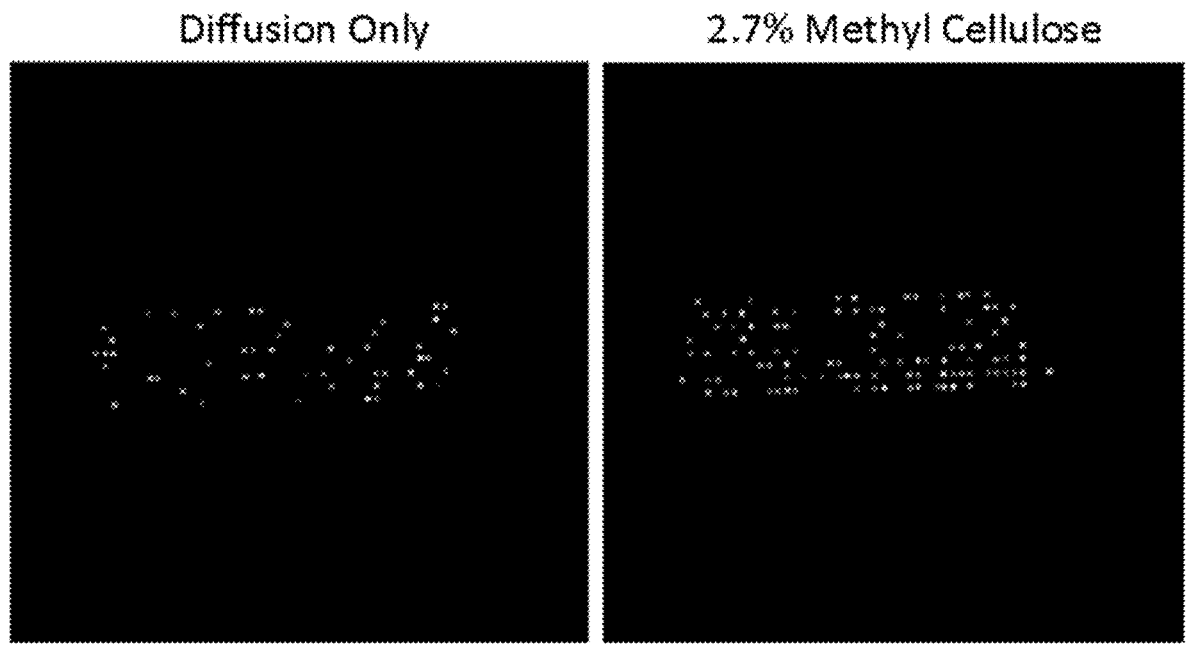

FIG. 9 depicts DNA fluorescence imaging of a nucleic acid sample loaded into a sample well by diffusion (left) and a nucleic acid sample loaded into a sample well in the presence of a crowding agent (right).

Figure 10:
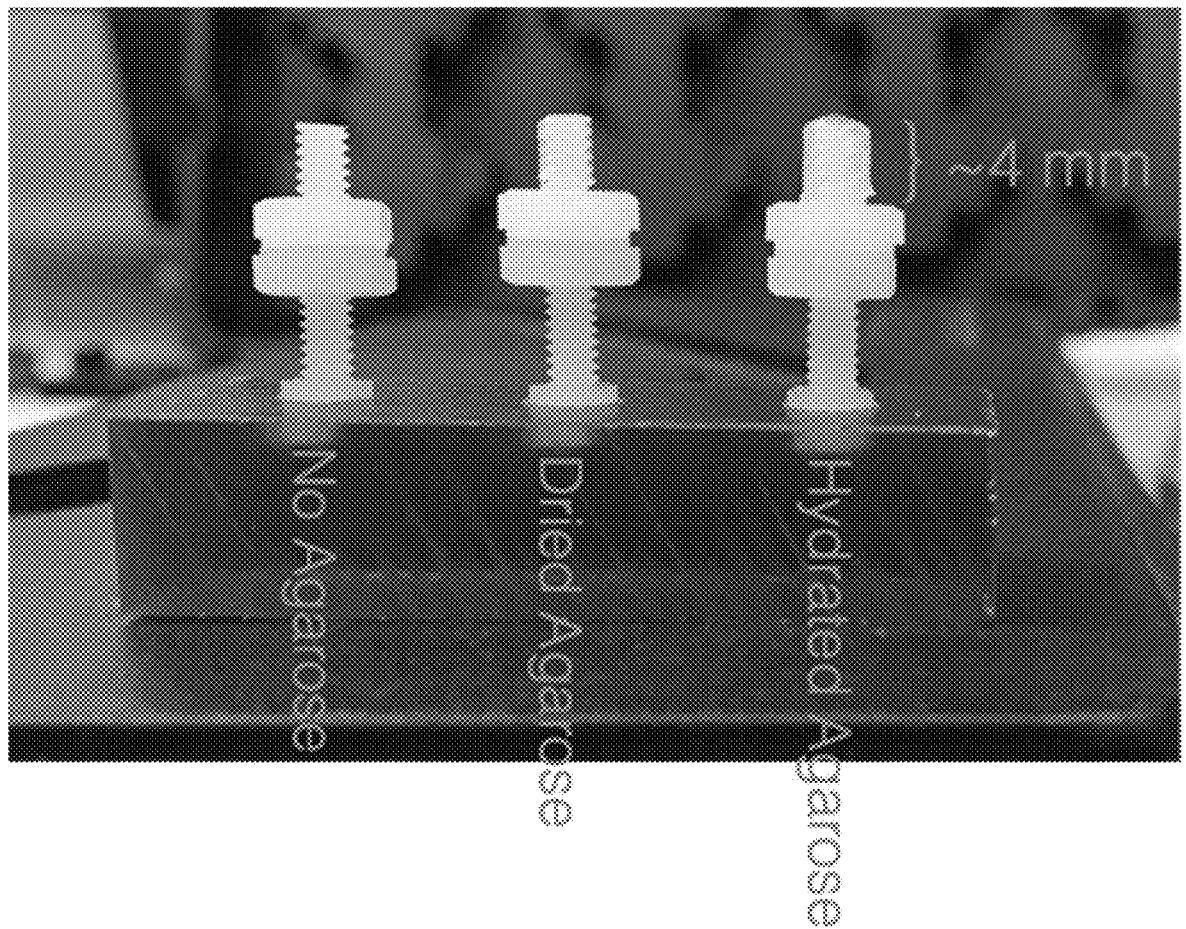

FIG. 10 depicts an experimental setup that demonstrated proof of concept for a solid state crowding agent.

DETAILED DESCRIPTION

Among other aspects, the present disclosure provides methods and compositions for loading a molecule of interest into a sample well. In some aspects, techniques described herein involve steps of contacting a sample that comprises a molecule of interest to a surface of a solid support comprising a sample well (e.g., in an integrated device comprising a sample well having a bottom surface distal to the surface of the integrated device). In some embodiments, the sample may be contacted with a crowding agent that directs the molecule of interest toward the bottom surface of the sample well. In some embodiments, the bottom surface of the sample well comprises a coupling group configured to bind the molecule of interest. In this way, the molecule of interest may become bound to the bottom surface of the sample well through the coupling group. In some embodiments, the sample further comprises a condensing agent that causes the molecule of interest to assume a condensed structure relative to its structure in absence of the condensing agent. In some embodiments, the molecule of interest comprises a sequencing template.

In some aspects, methods and compositions described herein may be useful in techniques that allow for the detection of an individual molecule or particle in a sample. The individual molecule may be, by way of example and not limitation, an amino acid, a polypeptide, a nucleotide, and/or a nucleic acid. For example, in some embodiments, methods and compositions provided in the present disclosure may be used in conjunction with single molecule nucleic acid sequencing technologies. Single molecule nucleic acid sequencing allows for the determination of a sequence of a single template nucleic acid molecule by monitoring, in real time, the extension of a nucleic acid molecule that is complementary to the template nucleic acid.

In certain techniques, single molecule nucleic acid sequencing is performed by isolating single sequencing templates within each of a plurality of sample wells. In many applications, however, the total volume of these sample wells relative to the total sample volume is considerably low. Additionally, the concentration of sequencing template in a sample that is required to minimize multiple templates in single sample wells is often so low that the kinetics of loading the sequencing templates into the sample wells can severely limit the amount of successfully loaded and sufficiently active complexes. The inventors have recognized and appreciated that these and other limitations may be overcome by utilizing specific reagents as part of the sequencing template loading process.

Accordingly, having recognized the need for improved sequencing template preparation and sequencing template loading practices, the inventors have developed techniques that make use of crowding agents to effectively reduce bulk volume of a sample such that sequencing templates are excluded from the bulk volume and driven into sample wells. The inventors have further recognized and appreciated that the crowding agents described herein provide advantages beyond the aforementioned considerations regarding sequencing template size.

In some embodiments, the disclosure provides methods of loading a molecule of interest into a sample well by contacting a sample having the molecule of interest to a surface of an integrated device. In some embodiments, the integrated device comprises the sample well. For example, FIG. 1 is a cross-sectional view of a sample well 108 comprised by an integrated device 100, according to some non-limiting embodiments of the present application. A sample well 108 may comprise a small volume or region at a surface of an integrated device 110, which is distal to a bottom surface 112 of sample well 108. Sample well 108 may be configured to receive a sample comprising a molecule of interest 191, which can be retained at bottom surface 112 of sample well 108. Bottom surface 112 of sample well 108 comprises one or more coupling groups that bind to molecule of interest 191, at least temporarily for a duration of time. Bottom surface 112 of sample well 108 may have one or more materials that provide selectivity for molecule of interest 191 to adhere to the bottom surface rather than the side walls 190 of sample well 108. In some embodiments, bottom surface 112 and side walls 190 of sample well 108 may be prepared (e.g., passivated, functionalized, etc.) using techniques described herein or methods known in the art.

In some embodiments, molecule of interest 191 may be disposed within sample well 108 through a top aperture that is distal to bottom surface 112 of sample well 108. The top aperture may be configured to reduce ambient light or stray light from illuminating molecule of interest 191 within sample well 108. The top aperture may have a width $W_A$, as measured at a surface of an integrated device 110, that is in the range of 50 nm and 300 nm, or any value or range of values within that range. Sample well 108 may have a depth $d_W$ between bottom surface 112 and an interface 127 between a top cladding 118 and a metal layer 122. Depth $d_W$ may provide a suitable distance between a molecule of interest positioned at bottom surface 112 and metal layer 122. Depth $d_W$ may impact the timing of photon emission events of a marker (e.g., lifetime) associated with molecule of interest 191. Accordingly, depth $d_W$ may allow for distinguishing among different markers in sample well 108 based on timing characteristics associated with the individual lifetimes of the different markers. In some embodiments, depth $d_W$ of sample well 108 may impact the amount of excitation energy received. Depth $d_W$ may be in the range of 50 nm to 350 nm, or any value or range of values within that range. In some embodiments, depth $d_W$ is between 95 nm and 150 nm. In some embodiments, depth $d_W$ is between 150 nm and 350 nm. In some embodiments, depth $d_W$ is between 200 nm and 325 nm. In some embodiments, depth $d_W$ is between 250 nm and 300 nm. In some embodiments, depth $d_W$ is approximately 270 nm.

In various embodiments, sample well 108 may be arranged to receive excitation energy from a waveguide 116. Waveguide 116 may be configured to provide an optical mode that evanescently decays from the waveguide. In some embodiments, the evanescent field of the mode may overlap, at least in part, with sample well 108. In this way, molecule of interest 191 within sample well 108 may receive excitation energy through the evanescent field of the optical mode.

Integrated device 100 may include metal layer 122 over top cladding 118. Metal layer 122 may act as a reflector for emission energy emitted by a sample in a sample well and may improve detection of emission energy by reflecting emission energy towards a sensor of the integrated device. Metal layer 122 may act to reduce the background signal due to photons that do not originate within the sample well. Metal layer 122 may comprise one or more sub-layers. Examples of suitable materials to be used as layers of a metal layer may include aluminum, copper, titanium, and titanium nitride. As shown in FIG. 1, metal layer 122 includes first sub-layer 124, second sub-layer 126, and third sub-layer 128. The thickness of the first sub-layer may be in the range of 30 nm to 165 nm, or any value or range of values within that range. The thickness of the second sub-layer may be in the range of 5 nm to 100 nm, or any value or range of values within that range. In some embodiments, the thickness of the second sub-layer may be approximately 10 nm. The third sub-layer may have a thickness in the range of 5 nm to 100 nm, or any value or range of values within that range. In some embodiments, the third sub-layer may have a thickness of approximately 30 nm.

Sample well 108 may have one or more sidewalls covered, at least partially, with a sidewall spacer on sidewalls 190. The composition of a sidewall spacer may be such that the sidewalls 190 are configured to enable a certain type of interaction with molecule of interest 191. In some embodiments, a sidewall spacer may have a composition configured to passivate the sidewalls of sample well 108 to reduce the amount of molecule of interest 191 that adheres to the sidewalls 190. By coating only the sidewalls of the sample well with the spacer, a different type of interaction with molecule of interest 191 may be provided at a different area of sample well 108. A sidewall spacer may have a thickness in the range of 3 nm to 30 nm, or any value or range of values within that range. In some embodiments, a sidewall spacer may have a thickness of approximately 10 nm. Examples of suitable materials used to form a sidewall spacer include $TiO_2$, TiN, TiON, TaN, $Ta_2O_5$, $Zr_2O_5$, and $HfO_2$. In some embodiments, the sample well structure may have bottom surface 112 proximate to waveguide 116 that lacks spacer material on the sidewalls. The distance between the bottom surface and sidewall spacer may be in the range of 20 nm to 50 nm, or any value or range of values within that range. In this way, bottom surface 112 of the sample well is closer to waveguide 116, thus improving coupling of excitation energy and reducing the impact of the metal stack on optical loss of excitation energy.

According to some embodiments, a sample well may be comprised by an integrated device. In some embodiments, the integrated device comprises a plurality, or an "array," of sample wells. For example, FIG. 2 depicts a cross-sectional view of an integrated device 200 comprising a plurality of sample wells. As shown, integrated device 200 comprises a top cladding 218 between a waveguide 216 and a metal layer 222, where top cladding 218 separates waveguide 216 and metal layer 222 by a maximum distance $h_c$. Top cladding 218 may have one or more regions that have a dimension less than $h_c$ and include one or more sample wells. Such a region may be considered an array of suitable size and shape to include one or more sample wells of the integrated device. Integrated device 200 includes array 220 where top cladding 218 separates waveguide 216 and metal layer 222 by a distance that is less than $h_c$. Array 220 may have an area in a plane perpendicular to the view shown in FIG. 2 of any suitable size and shape to include a desired number of sample wells. In some embodiments, array 220 may have a rectangular shape (e.g., square). Array 220 may have a plurality of sample wells, including sample wells $208_1$, $208_2$, $208_3$, $208_4$, $208_5$, and $208_6$. While FIG. 2 depicts six sample wells, the application is not limited in this respect and any suitable number of sample wells may be formed in an array. An array can have any suitable size or shape. In some embodiments, an array is in a trench region.

Aspects of the techniques described herein involve contacting a sample to a surface of an integrated device. As shown in FIG. 2, integrated device 200 contains a plurality of sample wells in an array 220 that may be formed at a depressed surface of the integrated device $210_1$. Accordingly, in some embodiments, a sample may be contacted to a depressed surface of an integrated device $210_1$ in an array of the integrated device. In yet other embodiments, a sample may be contacted to a surface of an integrated device that is not in depressed region (e.g., not in a trench region). For example, as depicted in FIG. 2, a sample may be contacted to a surface of an integrated device $210_2$. It should be appreciated that while FIG. 2 depicts a plurality of sample wells in a depressed region (e.g., a bathtub) of an integrated device, an integrated device may comprise a plurality of sample wells without also comprising a depressed region.

Integrated device 200 may include metal layer 222 over top cladding 218. Metal layer 222 may act as a reflector for emission energy emitted by a sample in a sample well and may improve detection of emission energy by reflecting emission energy towards a sensor of the integrated device. Metal layer 222 may act to reduce the background signal due to photons that do not originate within the sample well. Metal layer 222 may comprise one or more sub-layers. Examples of suitable materials to be used as a metal layer include aluminum, titanium, and titanium nitride. Metal layer 222 may have one or more discontinuities corresponding to the etched portions of top cladding 218 to form sample wells $208_1$, $208_2$, $208_3$, $208_4$, $208_5$, and $208_6$. In some embodiments, a plurality of depressed regions (e.g., trench regions) of the type described herein may be formed in an integrated device, for example, to reduce optical loss due to the interaction of the optical mode traveling down waveguide 216 and metal layer 222. In some embodiments, an integrated device may include a depressed region for a single sample well. The integrated device may have multiple depressed regions in the top cladding where each depressed region corresponds to one sample well.

In certain techniques, it is preferable for a single sample well to comprise a single molecule of interest (e.g., a single sequencing template). Accordingly, in some embodiments, when loading a sample that comprises, for example, a sequencing template, into sample wells by introducing the sample onto an integrated device comprising an array of sample wells, care should be taken to avoid oversaturating the integrated device with a high concentration of the sequencing template. In such embodiments, it is often advisable to load sample wells using samples having a dilute concentration of sequencing template.

Without wishing to be bound by theory, it is postulated that the distribution of sequencing templates in a sample of dilute concentration across an array of sample wells is best modeled by a Poisson distribution. This discrete probability distribution predicts that approximately 37% of the sample wells in an array will contain one sequencing template, with the remaining wells containing either zero or multiple sequencing templates. In practice, achieving 37% single occupancy across an array of sample wells can be complicated by any number of chemical and/or mechanical variables. The inventors have recognized and appreciated that the techniques described herein, e.g., loading with a crowding agent, advantageously increase the percentage of single occupancy across an array of sample wells.

In some embodiments, methods and compositions described herein are capable of achieving single occupancy of molecules of interest in an array of sample wells that is comparable to, approximately the same as, or greater than the amount predicted by Poisson statistics. Accordingly, without wishing to be bound by theory, methods and compositions of the present application may be used with loading techniques that proceed via a non-random mechanism that skews a random distribution to produce a percentage of single loaded sample wells in excess of a Poisson distribution. For example, in some embodiments, methods and compositions of the present disclosure can achieve single occupancy of molecules of interest in approximately 20%, approximately 25%, approximately 30%, approximately 35%, approximately 37%, approximately 40%, approximately 45%, approximately 50%, approximately 60%, approximately 70%, approximately 80%, approximately 90%, approximately 95%, approximately 99%, or approximately 100% of sample wells in an array. However, in some embodiments, methods and compositions of the present disclosure are useful to increase the rate at which molecules of interest occupy an array of sample wells in a distribution (e.g., of single occupancy) that would be predicted by Poisson statistics.

Among other aspects, techniques described herein relate to the use of a crowding agent for loading a molecule of interest into a sample well. As described herein, a crowding agent may effectively exclude a molecule of interest (e.g., a sequencing template) from bulk solvent of a sample. A non-limiting example of this effect is depicted in FIGS. 3A and 3B. As shown in FIG. 3A, an integrated device $300_1$ having an array 320 comprising a plurality of sample wells may be contacted with a sample $340_1$ having a molecule of interest $390_1$. In some embodiments, methods of the disclosure are useful for loading molecules of interest into sample wells of extremely small volumes. For example, in some embodiments, the capacity of an array (e.g., in a trench region) in an integrated device and all sample wells therein is approximately $20\times10^{-6}$ L, with each sample well having a volume of approximately $3\times10^{-18}$ L. In some embodiments, an array (e.g., in a trench region) in an integrated device contains 512,000 samples wells. Accordingly, in some embodiments, the total volume of all sample wells in an array accounts for approximately 0.00000768% of the capacity for a sample. As depicted in FIG. 3A, sample $340_1$ having molecule of interest $390_1$ loaded in the absence of a crowding agent, and having a theoretically even distribution of molecule of interest $390_1$ in the bulk volume $342_1$ of sample $340_1$, would result in a fraction of sample wells capable of receiving a successfully loaded molecule of interest $391_1$.

FIG. 3B illustrates the effects of a crowding agent with respect to successfully loaded samples. An integrated device $300_2$ having an array comprising a plurality of sample wells may be contacted with a sample $340_2$ having a molecule of interest $390_2$. The sample $340_2$ may further comprise a crowding agent 350. As shown, the inclusion of crowding agent 350 may produce a volume exclusion effect that excludes molecule of interest $390_2$ from the bulk volume $342_2$ of sample $340_2$, which drives molecule of interest $390_2$ into a sample well. As a result, a much greater percentage of sample wells are capable of receiving a successfully loaded molecule of interest $391_2$. Thus, in some embodiments, crowding agents may produce a thermodynamic driving force that effectively increases the concentration of the molecule of interest at the surface of an integrated device. In some embodiments, crowding agents may decrease loading time by having a kinetic effect that accelerates the movement of the molecules of interest into the sample wells.

The inventors have further recognized and appreciated that the crowding agents described herein allow a molecule of interest, e.g., a sequencing template, to be loaded into a sample well of greater depth than conventional sample wells used in single molecule sequencing (e.g., greater than 150 nm, greater than 200 nm, greater than 250 nm, etc.). For example, in some embodiments, the molecule of interest is bound to the sample well at a bottom surface of the sample well. In some embodiments, the bottom surface is distal to the surface of an integrated device comprising the sample well, such that the distance between the bottom surface and the surface of the integrated device approximates the depth of the sample well. In some embodiments, sample wells of greater depth may be advantageously paired with techniques that utilize optical components.

In some embodiments, single molecule sequencing comprises the use of optical systems and sensors. For example, in some embodiments, a sequencing reaction is monitored in real time by directing light into a sample well on an integrated device and detecting light emitted from the sample well. In some embodiments, a source of light directing light into the sample well is positioned at or beneath the bottom of the sample well and a photodetector is used to detect emissions from the sample well (e.g., emissions related to one or more component or event associated with the sequencing reaction). In such embodiments, light may interact with one or more features at or near the surface of the integrated device to negatively affect the ability to monitor the sequencing reaction. In some embodiments, these hindrances (e.g., background noise, optical loss) may be reduced or eliminated by increasing sample well depth.

As the depth of the sample well is increased, however, the increased distance between the bottom surface of the sample well and the surface of the integrated device necessarily creates a greater distance through which a molecule of interest must diffuse to reach the bottom surface (e.g., to consequently bind to the bottom surface). As such, the advantages provided by increased sample well depth may entail certain limitations relating to loading efficiency (e.g., achieving high single occupancy across an array of sample wells). The inventors have recognized and appreciated that the techniques described herein, e.g., loading with a crowding agent, are superior for loading molecules of interest (e.g., sequencing templates) into deep sample wells when compared to loading by un-augmented diffusion alone.

Crowding Agents

As used herein, a "crowding agent" is a compound or molecule that allows for, enhances, or facilitates molecular crowding. Without wishing to be bound by any particular mechanism, it is suggested that crowding agents reduce the volume of solvent that is available for other macromolecules. This excluded volume effect limits the volume accessible to macromolecules as a result of non-specific interactions, such as steric repulsion, with the crowding agent. Accordingly, in some embodiments, a crowding agent may be referred to as a "volume excluder" or "volume excluding agent." In some embodiments, the crowding agent is inert with respect to other components in the same solution. For example, in some embodiments, the crowding agent selectively excludes a molecule of interest from a portion of total sample volume without excluding other components in the solution from the portion or retaining other components in the solution in the portion. In some embodiments, the crowding agent is a hydrophilic compound. In some embodiments, the crowding agent does not interfere with reactions occurring in the same solution. The crowding agent is contemplated to function in a variety of ways with the methods and compositions described herein, e.g., as illustrated in FIG. 4.

FIG. 4 generically illustrates an example of the effects of a crowding agent in a sample with a molecule of interest. Panels $400_1$ and $400_2$ each depict a sample having a molecule of interest 491 and an agent 450. As shown, the agents $450_1$ in panel $400_1$ are relatively dispersed throughout the sample compared to the agents $450_2$ in panel $400_2$. Accordingly, panel $400_1$ provides a simplified example of a sample in which the molecule of interest 491 can freely access bulk volume $442_1$ not already occupied by an agent $450_1$. By comparison, the agents $450_2$ in panel $400_2$ are shown to associate such that an interstitial volume 444 is formed (shaded region). As shown, where the size of the molecule of interest 491 exceeds the interstitial volume 444, this region becomes inaccessible to the molecule of interest 491. As a result, the amount of accessible bulk volume $442_2$ in the sample of panel $400_2$ is less than the amount of accessible bulk volume $442_1$ in the sample of panel $400_2$. This effect, which relates to the exclusion of the molecule of interest 491 from a volume in a sample, can be referred to as volume exclusion. It should be appreciated, however, that a volume exclusion effect can give rise to a molecular crowding effect, and vice versa.

FIG. 4 further illustrates an example of the excluded volume effect in the context of a sample well. Panels $401_1$ and $401_2$ each depict a sample well having a bottom surface that comprises a coupling group 493 configured to bind the molecule of interest 491. Further, each of panels $401_1$ and $401_2$ depict a sample well that has been contacted with a sample comprising a molecule of interest 491. The sample illustrated in panel $401_2$ further comprises a crowding agent 450. As shown, the crowding agent 450 decreases the amount of bulk volume 442 accessible to the molecule of interest 491. As a result of the interstitial volume 444 of the crowding agent 450 that is inaccessible to the molecule of interest 491, the molecule of interest is thermodynamically driven toward the top aperture of the sample well. In some embodiments, as shown in panel $401_2$, the crowding agent 450 can comprise a polymeric molecule that forms entangled structures that ties up a portion of the sample to decrease bulk volume 442 that is accessible to the molecule of interest 491. Without wishing to be bound by theory, it is postulated that the structures formed by a crowding agent 450 in a sample limit the extent to which the crowding agent 450 may enter a sample well. Consequently, the interstitial volume 444 would occupy a region external to the sample well to effectively increase the concentration of the molecule of interest at a top aperture of a sample well that is distal to the bottom surface. The increased local concentration of molecule of interest 491 at the top aperture of the sample well may result in a greater probability that the molecule of interest 491 is bound to the bottom surface through the coupling group 493.

Accordingly, in some embodiments, a crowding agent selectively excludes a molecule of interest relative to solvent molecules and/or other components in solution. In some embodiments, a solution comprising the molecule of interest has been contacted to a surface of an integrated device such that the molecule of interest occupies a first volume at the surface of the integrated device. In some embodiments, a solution comprising the crowding agent is contacted to a surface of the first volume such that the crowding agent occupies a second volume at the surface of the first volume. Where the crowding agent selectively excludes the molecule of interest relative to solvent molecules and/or other components, the molecule of interest is excluded from the second volume while solvent and/or other components of the first volume are not excluded. As a result, the selective exclusion decreases the first volume with a concomitant increase in the second volume. It should be appreciated that, in some embodiments, the other components in the first volume (e.g., salts, buffers, etc.) can vary in the extent to which the second volume occupied by the crowding agent is accessible. For example, relative size, charge, and other chemical and physical properties of crowding agents and the components can affect the extent to which the components can be selectively excluded or preferentially retained by the crowding agent. Because a molecule of interest can included reaction components (e.g., sequencing templates), it is important that the crowding agent does not preferentially retain other components in solution that might be necessary to stabilize the molecule of interest (e.g., buffering agents, reducing agents, etc.).

In some embodiments, the crowding agent attracts water and allows molecules other than water to aggregate. In some embodiments, the crowding agent binds to and/or ties up water in a solution to exclude a macromolecule in the solution. In some embodiments, the crowding agent excludes a molecule of interest. In some embodiments, the crowding agent excludes a sequencing template. In some embodiments, the crowding agent restricts the available volume in a sample well. In some embodiments, the crowding agent promotes single occupancy of the molecule of interest in the sample well. In some embodiments, the crowding agent compacts the molecule of interest, such as a sequencing template, to allow larger sequencing templates to be loaded into the sample well. In some embodiments, the crowding agent promotes phase separation. In some embodiments, the crowding agent comprises randomly coiled polymers. In some embodiments, the crowding agent excludes contaminants (e.g., cellular debris) such that limited or no sample purification is necessary prior to loading of the molecule of interest. For example, in some embodiments, the crowding agent allows a dilute component of an impure sample (e.g., blood, urine, lysed cells, etc.) to be loaded more effectively than the impure sample loaded in absence of the crowding agent. In some embodiments, the crowding agent exerts osmotic pressure. In some embodiments, the crowding agent facilitates the loading of molecules of interest into deep sample wells. In some embodiments, the crowding agent promotes faster loading of sample wells. For example, in some embodiments, the crowding agent decreases the time required to incubate a sample on an integrated device comprising sample wells.

Crowding agents are known in the art and have previously been used to simulate the effects of intracellular macromolecular crowding in vitro (see, for example, Tokuriki, N., et al. (2004) *Protein Sci.* 13(1):125-133; Kuznetsova, I. M., et al. (2014) *Int. J. Mol. Sci.* 15:23090-23140; Phillip, Y., et al. (2009) *Biophys. J.* 97(3):875-885; Bhat, R., et al. (1992) *Protein Sci.* 1:1133-1143; Christiansen, A., et al. (2013) *Biophys. Rev.* 5(2):137-145; Aumiller, W. M., et al. (2014) *J. Phys. Chem. B* 118(36):10624-10632; the contents of each of which are incorporated herein by reference).

In some embodiments, a crowding agent is selected such that it stays (e.g., preferentially) in a sample reservoir as opposed to migrating into sample wells. In some embodiments, this promotes a thermodynamic driving force that drives the loading of sample components (e.g., DNA-polymerase complex) into the sample wells. In some embodiments, lower viscosity crowding agents such as Ficoll or linear polyvinylpyrrolidone have high mobility and poor localization relative to higher viscosity agents and are not as effective as the higher viscosity agents. However, lower viscosity agents may be useful in some contexts.

In some embodiments, a crowding agent is applied using a crowding agent solution having a viscosity of 1 mPa·s or higher (e.g., around or higher than 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mPa·s, or higher or intermediate ranges of viscosity). In some embodiments, a 2.7% composition of 63,000 Da methylcellulose has a viscosity of approximately 6.9 mPa·s. In some embodiments, useful viscosities for pipetting crowding agents can be between 1,000 and 15,000 mPa·s. However, in some embodiments the upper viscosity range of an agent can be limited by practical pipetting considerations. For example, solutions having viscosities of around 12,000 mPa·s or higher can be difficult to pipette and in some embodiments, a crowding agent solution is added at a concentration that has a viscosity of 12,000 mPa·s or lower.

In some embodiments, smaller (e.g., shorter) agents having lower viscosities can be applied at higher concentrations than larger (e.g., longer) agents to achieve similar viscosities in a loading composition. However, in some embodiments shorter molecules are less efficient crowding agents and can also more easily migrate from a sample reservoir into a sample well.

In some embodiments, a viscosity of a crowding agent preparation can be calculated based on a viscosity-concentration equation such as mPa·s=$(\%\times 0.747+1)^8$ (e.g., for Methocel, cellulose ether, from Dow).

In some embodiments, the shape and size of a crowding agent can impact its effectiveness. In some embodiments, the exclusion of a DNA/polymerase complex is particularly effective using similar sized crowding agents (e.g., crowding agents ranging from 2 to 3 times smaller to 2 to 3 times larger). In some embodiments, crowding agents having shapes that promote entangled, higher viscosity solutions are useful.

In some embodiments, the crowding agent is a water soluble macromolecular material. In some embodiments, suitable macromolecular materials broadly comprise biocompatible natural or synthetic polymers do not specifically interact with the other reagents in a mixture. In some embodiments, the crowding agent is an inert macromolecule, such as an inert polypeptide or an inert nucleic acid. In some embodiments, the crowding agent is a linear polymer.

In some embodiments, the crowding agent is a polysaccharide. In some embodiments, the crowding agent is a cellulose molecule. In some embodiments, the crowding agent is methyl cellulose. In some embodiments, the crowding agent is a cellulose molecule selected from the group consisting of ethyl cellulose, ethyl methyl cellulose, hydroxyethyl cellulose, hydroxypropyl cellulose, hydroxyethyl methyl cellulose, hydroxypropyl methyl cellulose, ethyl hydroxyethyl cellulose, carboxymethyl cellulose, and derivatives and combinations thereof. In some embodiments, the crowding agent is a Ficoll polymer.

In some embodiments, a crowding agent, for example a cellulose crowding agent (e.g., Methocel MC of 63,000) has an average molecular weight of 50,000 to 500,000 Da (e.g., around 50 to 100 kDa, 100 to 200 kDa, 200 to 300 kDa, 300 to 400 kDa, 400 to 500 kDa or higher). In some embodiments, "average molecular weight" as used herein refers to the number average molecular weight (Mn) of a crowding agent in solution. In some embodiments, a cellulose crowding agent has a number average molecular weight of 50,000 to 500,000 Da. In some embodiments, the number average molecular weight of a cellulose crowding agent is approximately 63 kDa. In some embodiments the number average molecular weight of a cellulose crowding agent is between about 20 and 120 kDa, between about 26 and 110 kDa, between about 41 and 86 kDa, between about 50 and 75 kDa, or between about 60 and 70 kDa.

Average molecular weight, in some embodiments, can be determined according to manufacturer specifications. In some embodiments, average molecular weight of a cellulose crowding agent can be calculated or approximated based on the proportional relationship between apparent viscosity and the molecular weight or chain length of the specific cellulose compound. In view of this proportionality, known reference values can be used to determine average molecular weight by measuring apparent viscosity of an aqueous solution with a known concentration of cellulose at a known temperature. For example, in some embodiments, average molecular weight of a Methocel cellulose composition can be obtained by measuring viscosity values for a 2% (w/v) solution of cellulose at 20° C. (e.g., using measurement methods set forth in ASTM monographs D1347 and D2363) and comparing the measured values to known values provided by the manufacturer (e.g., as described in *METHOCEL Cellulose Ethers Technical Handbook* (The DOW Chemical Company); Form No. 192-01062-0902 AMS, published September 2002).

In some embodiments, the crowding agent is a polyether compound. In some embodiments, the crowding agent is a polyether compound selected from the group consisting of polyethylene glycol (e.g., PEG 200 and up, including PEG 20,000 and up), polypropylene glycol, paraformaldehyde, polytetramethylene glycol, polyphenyl ether, and derivatives and combinations thereof. In some embodiments, the crowding agent is selected from the group consisting of bovine plasma albumin, glycogen, dextran, and derivatives and combinations thereof. In some embodiments, the crowding agent is a polyamide. In some embodiments, the crowding agent is a cyclic polyamide (e.g., polyvinylpyrrolidone).

In some embodiments, the crowding agent is provided as a solution. In some embodiments, concentration of the crowding agent in the solution is about 0.6% by weight. In some embodiments, concentration of the crowding agent in the solution is about 0.9% by weight. In some embodiments, concentration of the crowding agent in the solution being added is about 1.8% by weight. In some embodiments, concentration of the crowding agent in the solution is about 2.0% by weight. In some embodiments, concentration of the crowding agent in the solution is about 2.3% by weight. In some embodiments, the crowding agent is present in the solution between about 0.1% by weight to about 1.0% by weight, between about 1.0% by weight to about 2.0% by weight, between about 2.0% by weight to about 3.0% by weight, between about 3.0% by weight to about 4.0% by weight, between about 4.0% by weight to about 5.0% by weight, between about 5.0% by weight to about 6.0% by weight, between about 6.0% by weight to about 7.0% by weight, between about 7.0% by weight to about 8.0% by weight, between about 8.0% by weight to about 9.0% by weight, between about 9.0% by weight to about 10.0% by weight, between about 10.0% by weight to about 15.0% by weight, between about 10% by weight to about 11% by weight, between about 11% by weight to about 12% by weight, between about 12% by weight to about 13% by weight, between about 13% by weight to about 14% by weight, or between about 14% by weight to about 15% by weight, between about 15.0% by weight to about 20.0% by weight, or greater.

In some embodiments, a solution of crowding agent is added in a volume that is of the same order of magnitude (e.g., 1 to 3 times smaller to 1 to 3 times larger) as the volume of the sample solution (e.g., in a loading buffer). In some embodiments, a 2.7% solution of crowding agent (e.g., Methocel MC) is pipetted over an approximately equivalent volume of sample in loading buffer. In some embodiments, a 1.8% solution of crowding agent is pipetted over an approximately equivalent volume of sample in loading buffer. In some embodiments, a 1.2% solution of crowding agent is pipetted over an approximately equivalent volume of sample in loading buffer. In some embodiments, a 0.9% solution of crowding agent is pipetted over an approximately equivalent volume of sample in loading buffer. In some embodiments, a 0.6% solution of crowding agent is pipetted over an approximately equivalent volume of sample in loading buffer.

In some embodiments, a crowding agent solution is placed over a sample solution without mixing. However, the solutions also can be mixed in some embodiments.

In some embodiments, a crowding agent is provided in the form of a gel (e.g., a hydrophilic gel) that can be placed in direct contact with a sample solution (e.g., in a sample reservoir). Gels can be applied (e.g., in the form of a gel plug) without being limited by pipetting considerations and higher concentrations and viscosities of crowding agent can be used in the form of a gel.

In some embodiments, the crowding agent is provided in a solid state. For example, in some embodiments, the crowding agent is provided as a film. In some embodiments, the crowding agent may be provided as a fibrous material, a membranous material, an adhesive material, a composite material, a laminate material, or some combination thereof. In some embodiments, the film may comprise a synthetic and/or natural material suitable for use with the methods and compositions described herein. In some embodiments, the film is a material selected from a crosslinked gel or a dehydrated solution. In some embodiments, the film comprises polyacrylamide, dextran, agarose, or some combination or variant thereof. In some embodiments, a solid state crowding agent (e.g., a film) advantageously takes up water in the bulk volume of a sample while preferentially excluding a molecule of interest (e.g., a sequencing template). Accordingly, it should be appreciated that any such suitable agent may be used as a solid state crowding agent in the methods provided herein.

Condensing Agents

As used herein, "condensing agent" refers to any natural or synthetic compound, which when combined with a molecule of interest causes the molecule of interest to assume a condensed structure relative to its structure in absence of the condensing agent. For example, in a given sample, the molecule of interest occupies a smaller volume in the presence of the condensing agent than the same sample lacking the condensing agent. Accordingly, in some embodiments, a condensing agent decreases occupancy volume of the molecule of interest in the sample. In some embodiments, a condensing agent interacts with the molecule of interest such that the molecule adopts a compacted structure that occupies a smaller fraction of the total volume in a sample. In some embodiments, a condensing agent interacts with the molecule of interest to reduce the pervaded volume of the molecule. By introducing a condensing agent, the molecule may have a smaller pervaded volume than if the condensing agent was absent and the molecule may more readily load into a sample well because of its smaller pervaded volume. In some embodiments, the condensing agent is inert with respect to other components in the same solution. In some embodiments, the condensing agent does not interfere with reactions occurring in the same solution.

FIG. 5 generically illustrates an example of the effects of a condensing agent in a sample with a molecule of interest. For example, scheme 500 depicts a process in which a molecule of interest 591 is contacted with a condensing agent 530. A molecule of interest $591_1$ is shown as occupying an initial volume $V_1$ approximated by a sphere of radius $r_1$. After being contacted with a condensing agent 530, the condensed molecule of interest $591_2$ is shown as occupying a condensed volume $V_2$ approximated by a sphere of radius $r_2$. In some embodiments, initial volume $V_1$ and condensed volume $V_2$ refer to pervaded volumes of a molecule of interest $591_1$ and a condensed molecule of interest $591_2$, respectively. Accordingly, in some embodiments, a condensing agent 530 is configured to reduce the volume a molecule of interest 591 occupies in solution, which may be considered the pervaded volume of the molecule. By introducing a condensing agent, the molecule may have a smaller pervaded volume than if the condensing agent was absent and the molecule may more readily load into a sample well because of its smaller pervaded volume.

FIG. 5 further illustrates an example of the use of a condensing agent in the context of loading a molecule of interest into a sample well. Panels $501_1$ and $501_2$ each depict a sample well having a bottom surface that comprises a coupling group 593 configured to bind the molecule of interest 591. Further, each of panels $501_1$ and $501_2$ depict a sample well that has been contacted with a sample comprising a molecule of interest 591. The sample depicted in panel $501_1$ includes a molecule of interest $591_1$ that has not been contacted with a condensing agent, whereas the sample depicted in panel $501_2$ includes a condensed molecule of interest $591_2$ that has been contacted with a condensing agent. As shown, a condensed molecule of interest $591_2$ occupies a condensed volume relative to the molecule of interest $591_1$ shown in panel $501_1$. Accordingly, the decreased volume occupied by the condensed molecule of interest $591_2$ may result in a greater probability that the molecule of interest 591 is bound to the bottom surface through the coupling group 593. In some embodiments, a condensing agent may be advantageously utilized where it is desirable to load a molecule of interest 591 that occupies a relatively large volume into a sample well having a capacity of relatively small volume (e.g., a volume suitable for single molecule occupancy, such as a sample well of an array used for single molecule sequencing). In some embodiments, the condensing agent may be further utilized in combination with a crowding agent described herein. In such implementations, the net effect of a crowding agent decreasing accessible bulk volume of a sample and a crowding agent decreasing volume occupied by each molecule of interest results in sample well single occupancy that approximates or is greater than that predicted by Poisson statistics.

In some embodiments, the condensing agent is a nucleic acid condensing agent. Nucleic acid condensing agents can compact nucleic acids by a variety of mechanisms, including, but not limited to, volume exclusion and charge screening. Assays to evaluate the capability of an agent to condense nucleic acids are known in the art, e.g., as described in WO/1996/021036, the relevant content of which is incorporated herein by reference in its entirety. In some embodiments, a nucleic acid condensing agent interacts with nucleic acids via electrostatic charge-charge interactions to induce a collapsing of the nucleic acid structure (e.g., nucleic acid condensation). In some embodiments, a condensing agent can condense a nucleic acid as a result of one or more of the following: exerting osmotic pressure to bring segments of the helical structure together (e.g., molecular crowding effect), decreasing repulsive interactions between nucleic acid segments (e.g., by neutralizing phosphate charge), and increasing attractive interactions between nucleic acid segments. In some embodiments, attractive interactions between the DNA segments can be induced by multivalent cationic charged condensing agents.

In some embodiments, a condensing agent comprises a polycation. As used herein, a polycation refers generally to a compound having a plurality of positively charged sites. In some embodiments, the polycation is polycationic when present in a sample that includes a molecule of interest. For example, in some embodiments, conditions (e.g., pH, buffer capacity, ionic strength) in a sample comprising a molecule of interest are such that the condensing agent is polycationic in the sample. In some embodiments, the polycation is polycationic at physiological pH (e.g., pH≈7.4). In some embodiments, the polycation is a polymer of positively charged monomeric units, although some non-positively charged units may be present in the polymer. Examples of polycations include, in some embodiments, polyamines, such as spermine, spermidine, and putrescine. In some embodiments, the polycation comprises a polyamino acid, such as polyhistidine, polylysine, polyarginine, and polyornithine. Other basic peptides and small basic proteins are further contemplated for use as polycationic condensing agents (e.g., histones, protamines). For polycations composed of amino acids, either the L- or D-forms may be used. Basic amino acids include lysine, arginine, amino acid analogues such as ornithine and canaline, modified basic amino acids, such as homoarginine, and other modified amino acids modified to carry a positive charge, such as guanidinovalinate, and aminoethylcysteine. Additional examples of polycations include polyammoniums (e.g., Polybrene (hexadimethrine bromide)), lipids (e.g., DOTAP, DC-Chol/DOPE, DOGS/DOPE, and DOTMA/DOPE).

Oxygen Scavenging Sealants

In yet other aspects, the disclosure provides methods and compositions useful for protecting oxygen-sensitive systems and maintaining sample integrity. Biological and/or chemical reactions can often be sensitive to interactions with an external environment, e.g., susceptibility to evaporation and sensitivity to oxygen and/or other molecules in the external environment. Sealants have been previously used to protect sensitive reactions from deleterious interactions with an external environment. For example, mineral oil is often used to overlay samples during amplification by polymerase chain reaction (PCR). Accordingly, in some embodiments, methods of loading and sequencing described herein further comprise overlaying sequencing reactions with a sealant (e.g., mineral oil). The inventors have recognized and appreciated that certain compositions may be used, in place of or in addition to a conventional sealant, to confer additional protective effects for the sequencing reactions described herein. For example, in some embodiments, an oxygen scavenging sealant may be contacted to a sample.

Aspects of the disclosure relate to single molecule sequencing technologies. In some embodiments, single molecule sequencing comprises the use of optical systems. In such embodiments, optical systems may involve the use of excitation energies that may directly or indirectly be degradative to one or more components of a sequencing reaction. For example, in some embodiments, excitation energy can generate reactive oxygen species that may be damaging to the activity of a polymerizing enzyme in the sequencing reaction. The inventors have recognized and appreciated that an oxygen scavenging sealant minimizes the presence of reactive oxygen species while providing many of the same benefits as a conventional sealant (e.g., mineral oil).

In some embodiments, the oxygen scavenging sealant comprises an oxidizable agent and a catalyst. As used herein, an "oxidizable agent" is any agent capable of being oxidized. In some embodiments, oxidation of an oxidizable agent is mediated and/or accelerated by a catalyst. Accordingly, in some embodiments, oxygen scavenging proceeds through the oxidation of an oxidizable agent in a reaction or series of reactions catalyzed by a catalyst. In some embodiments, the oxygen scavenging sealant preferably is non-inhibitory (e.g., inert) with respect to the sequencing reaction. The sequencing reaction and reagents are protected from the oxygen scavenging components by phase separation (e.g., the scavengers agents remain segregated in oil phase and kept safely separate from the aqueous sequencing reagents).

In some embodiments, an oxidizable agent is an organic compound. In some embodiments, the oxidizable agent comprises at least one ethylenic bond. As used herein, an "ethylenic bond" is a carbon-carbon double bond. In some embodiments, the ethylenic bond may be either substituted or unsubstituted. In some embodiments, the ethylenic bond may be a terminal bond or an internal bond. In some embodiments, an ethylenic bond is contained within a ring structure. For example, in some embodiments, the ethylenic bond may be comprised by a 5-member or 6-member ring (e.g., a pentose ring or a hexose ring). In some embodiments, the organic compound may comprise oxygen-containing moieties. For example, oxygen-containing moieties can include, but are not limited to, esters, carboxylic acids, aldehydes, ethers, ketones, alcohols, peroxides, and/or hydroperoxides.

In some embodiments, oxidizable agents of the oxygen scavenging sealants provided herein are contemplated to include ascorbates and isoascorbates (as free acid, salts and derivatives), alkali metals, alkaline earth metals, or ammonium sulfite salts or mixtures thereof. In some embodiments, the oxidizable agent is a water insoluble ascorbate. In some embodiments, the oxidizable agent is formed by introducing an ascorbate or isoascorbate into the sealant as an ionic metal salt such as an alkali metal, an alkaline earth metal salt, an ester of an organic acid, or other derivatized ascorbate. In some embodiments, the oxygen scavenger ascorbate and/or isoascorbate component may be supplemented with other known reducing agents such as, e.g., a second ascorbate or isoascorbate, tannin, sulfite, and the like. In some embodiments, the ascorbate may be in the form of a C6-C22 fatty acid ester or diester which may be fully saturated or contain unsaturation in the hydrocarbon chain with a C10-C22 fatty acid ester. In some embodiments, the ascorbate ester may be, e.g., ascorbyl laurate, ascorbyl myristate, ascorbyl palmitate, ascorbyl stearate and the like.

In some embodiments, a scavenging agent is not very soluble. In some embodiments, a scavenging agent is provided in an oil (e.g., in an oil between saturation and 50% of saturation). In some embodiments, a scavenging agent (e.g., in oil) is selected based on its solubility (and/or provided at an appropriate concentration) to avoid partition into the underlying aqueous phase to an extent that could interfere with sequencing or other reactions.

As described herein, in some embodiments, an oxygen scavenging sealant comprises a catalyst. A wide range of catalysts are contemplated to be operative in the techniques described herein. Suitable catalysts include metal ions which can readily interconvert between at least two oxidation states. In some embodiments, the catalyst is a transition metal. For example, in some embodiments, the transition metal can be selected from the first, second, or third transition series of the Periodic Table. Suitable metals include, but are not limited to, manganese II or III, iron II or III, cobalt II or III, nickel II or III, copper I or II, rhodium II, III or IV, and ruthenium. It should be appreciated that the oxidation state of the metal when introduced is not necessarily that of the active form. In some embodiments, the transition metal is selected from scandium, titanium, vanadium, chromium, manganese, iron, cobalt, nickel, copper, and zinc. For example, in some embodiments, the catalyst comprises copper. In some embodiments, the transition metal is a lanthanide metal (e.g., lanthanum, cerium, praseodymium, neodymium, promethium, samarium, europium, gadolinium, terbium, dysprosium, holmium, erbium, thulium, ytterbium, or lutetium).

In some embodiments, a catalyst comprises a metal in the form of a salt, e.g., a metal ion and a counterion. Any suitable charged compound capable of complexing with a metal ion is contemplated to be used in the scavenging sealants described herein. In some embodiments, the counterion is selected from the group consisting of halide, sulfate, sulfite, sulfide, nitrate, nitrite, acetate, acetylacetonate, perchlorate, hydroxide, methoxide, and ethoxide. In some embodiments, the counterion is selected from the group consisting of laurate, myristate, palmitate, stearate, oleate, and linoleate.

In some embodiments, catalysts of the oxygen scavenging sealants provided herein are contemplated to include an oxidation catalyst that has limited or no water solubility. In some embodiments, the catalyst is provided in the form of an organic or inorganic transition metal compound which is substantially water insoluble. In some embodiments, the catalyst may be in the form of a salt or compound in which the transition metal is associated with other elements or groups by ionic or covalent bonds. In some embodiments, the catalyst may be in the form of a chelant, a complex, or an organic carboxylic fatty acid salt. In some embodiments, the transition metal compound is a compound having the transition metal in its highest oxidation state. In some embodiments, the oxygen scavenging sealant comprises a copper complex and an ascorbyl fatty acid ester.

Sample Loading

In some aspects, the present disclosure relates to methods and compositions useful for loading a molecule of interest (e.g., a sequencing template) into a sample well. For example, in some embodiments, the present disclosure provides methods and compositions useful for loading a sample comprising a molecule of interest into sample wells by introducing the sample onto a surface of an integrated device comprising sample wells. Sample loading by way of contacting a sample to a surface of an integrated device may be conducted by any number of suitable methods. In some embodiments, the sample comprising the molecule of interest is loaded by addition of the sample to the device by a practitioner, e.g., via a pipette, a dispenser, or any suitable fluid transfer device/system. In some embodiments, the sample comprising the molecule of interest is loaded by addition of the sample to the device via automated means (e.g., a robotic device/system). In some embodiments, the sample comprising the molecule of interest is loaded by addition of the sample to the device via one or more microfluidic channels.

In some embodiments, the molecule of interest can be delivered to an integrated device (e.g., an integrated device comprising sample wells, an array) by methods that are generally used to deliver molecules to the integrated device. For example, delivery methods can include suspending the molecule of interest in a fluid and flowing the resulting suspension into the sample wells of the integrated device. This can include simply pipetting the relevant suspension onto one or more regions of the integrated device, or can include more active flow methods, such as electro-direction or pressure-based fluid flow. In some embodiments, a sample comprising a molecule of interest is flowed into selected regions of the integrated device, e.g., where a particular molecule of interest is to be analyzed in a particular region of the integrated device. This can be accomplished by masking techniques (applying a mask to direct fluid flow), or by active flow methods such as electro-direction or pressure based fluid flow, including by ink-jet printing methods. Ink jet and other delivery methods for delivering nucleic acids and related reagents to arrays is found, e.g., in Kimmel and Oliver (Eds) (2006) DNA Microarrays Part A: Array Platforms & Wet-Bench Protocols, Volume 410 (*Methods in Enzymology*) ISBN-10: 0121828158; Lee (2002) Microdrop Generation (*Nano- and Microscience, Engineering, Technology and Medicine*) CRC Press ISBN-10: 084931559X; and Heller (2002) "DNA MICROARRAY TECHNOLOGY: Devices, Systems, and Applications" *Annual Review of Biomedical Engineering* 4: 129-153. In some embodiments, microfluidic flow can be used for molecule of interest delivery. Regions of an integrated device can also be selective targets of delivery simply by pipetting the relevant suspension into the correct region of the integrated device.

In some embodiments, methods of loading a sample comprising a molecule of interest into sample wells by introducing the sample onto an integrated device comprising sample wells may comprise one or more wash steps. For example, in some embodiments, the integrated device may be washed one or more times before and/or after introducing the sample onto the integrated device (e.g., before and/or after loading of the sample comprising the molecule of interest into sample wells of the integrated device). In some embodiments, the integrated device is washed with the same solution or buffer that is used to suspend the molecule of interest in the sample to be loaded. In some embodiments, the integrated device is washed with a nonionic surfactant (e.g., Tween 20). In some embodiments, the wash step comprises an incubation period during which the wash solution is allowed to incubate on the integrated device. In some embodiments, methods of loading described herein may be conducted without performing a wash step.

In some aspects, the disclosure provides methods of loading a molecule of interest (e.g., a sequencing template) into a sample well, comprising contacting the molecule of interest to a surface of an integrated device, and contacting the molecule of interest with a crowding agent and/or condensing agent. It should be appreciated that, in some embodiments, steps of contacting may be performed in any suitable order. For example, in some embodiments, the molecule of interest is contacted to the surface prior to being contacted with the crowding agent and/or condensing agent. In some embodiments, the molecule of interest may be contacted with (e.g., loaded onto) the integrated device, followed by an incubation period prior to being contacted with the crowding agent and/or condensing agent. In some embodiments, a condensing agent is present in the sample during such an incubation period. In some embodiments, the crowding agent and/or condensing agent is contacted with (e.g., loaded onto) the integrated device immediately or approximately soon after the molecule of interest has been contacted with (e.g., loaded onto) the integrated device. In some embodiments, the sample comprises the crowding agent and/or condensing agent prior to being contacted with the integrated device.

One example of an embodiment in which a sample is contacted to a surface of an integrated device is depicted in FIGS. 6A-6C. As shown in FIG. 6A, a sample 640 comprising a molecule of interest 690 is contacted to an integrated device having a plurality of sample wells. FIG. 6B depicts a layer 660 comprising a crowding agent 650 that has been added to sample 640. In some embodiments, layer 660 is allowed to incubate with sample 640 for a period of time, as described herein. In some embodiments, an incubation period may allow for crowding agent 650 to take up bulk volume (e.g., water) in sample 640 and exclude molecule of interest 690. FIG. 6C illustrates this volume exclusion effect that occurs following an incubation period, during which molecule of interest 690 is driven into the sample wells, whereby the sample wells have a higher probability of receiving a successfully loaded molecule of interest 691.

In yet other embodiments, the molecule of interest is contacted with the crowding agent prior to being contacted to the surface. For example, in some embodiments, the molecule of interest and the crowding agent may be mixed prior to being contacted with (e.g., loaded onto) the integrated device. In such embodiments, the molecule of interest and the crowding agent may be mixed and allowed to equilibrate for some period of time. In some embodiments, the molecule of interest and the crowding agent are mixed immediately prior to or approximately soon before being contacted with (e.g., loaded onto) the integrated device. In yet other embodiments, the molecule of interest is contacted to the surface and contacted with the crowding agent at approximately the same time. For example, in some embodiments, the molecule of interest and the crowding agent are contacted with (e.g., loaded onto) the integrated device at approximately the same time, such that the two components are mixed on the surface of the integrated device. In yet other embodiments, the molecule of interest is contacted with the crowding agent upon being contacted to the surface. For example, in some embodiments, the crowding agent is contacted with (e.g., loaded onto) the integrated device before the molecule of interest. In such embodiments, the crowding agent may be contacted with (e.g., loaded onto) the integrated device, followed by an incubation period prior to loading of the molecule of interest (e.g., via introduction of the molecule of interest onto the integrated device).

As described herein, the crowding agent generally facilitates loading of the molecule of interest into the sample well. In some embodiments, the crowding agent promotes attachment of the molecule of interest to a bottom surface of the sample well. Accordingly, in some embodiments, it may be desirable to incubate the molecule of interest-crowding agent mixture on the integrated device prior to initiation of the sequencing reaction. In some embodiments, the molecule of interest-crowding agent mixture is incubated on the integrated device prior to initiation of the sequencing reaction for approximately 1 minute to approximately 5 minutes, approximately 5 minutes to approximately 10 minutes, approximately 10 minutes to approximately 20 minutes, approximately 20 minutes to approximately 30 minutes, approximately 30 minutes to approximately 40 minutes, approximately 40 minutes to approximately 50 minutes, approximately 50 minutes to approximately 60 minutes, or approximately 60 minutes to approximately 90 minutes.

Following the incubation period, in some embodiments, excess volume may be removed from the integrated device. In some embodiments, the excess volume comprises the crowding agent and/or any molecule of interest that did not attach to a sample well. For example, following the successful loading of the molecules of interest depicted in FIG. 6C, FIG. 6D depicts an integrated device following removal of the excess volume comprising the crowding agent and molecules of interest which were not successfully loaded into the sample wells.

In some embodiments, the surface of the integrated device is washed one or more times following removal of the excess volume. As described herein, in some embodiments, the molecule of interest may participate in a reaction (e.g., a sequencing reaction) that can be initiated by any suitable technique described in the disclosure. For example, following the removal of excess volume depicted in FIG. 6D, FIG. 6E depicts the addition of a preparation 670 that comprises an element 652 that initiates a reaction results in an active molecule of interest 692. In some embodiments, the surface of the integrated device is washed one or more times preceding initiation of the reaction. In some embodiments, the surface of the integrated device is washed one or more times with the solution used to suspend the molecule of interest. In some embodiments, the surface of the integrated device is washed one or more times with the solution used to initiate the reaction. In some embodiments, the sequencing reaction is initiated following the optional removal and/or wash steps by any suitable means of initiation described elsewhere herein. For example, in some embodiments, the molecule of interest comprises a sequencing template that participates in a sequencing reaction. In such embodiments, the sequencing template may be advantageously "primed" for the sequencing reaction. In some embodiments, a sample comprising the sequencing template has most or all but one of the components necessary to initiate the sequencing reaction. Thus, the sequencing reaction may be initiated at an appropriate time by the addition of the necessary components to the sample. In some embodiments, the sequencing reaction is initiated by the addition of dNTPs to the sample. In some embodiments, the sequencing reaction is initiated by the addition of a metal cation (e.g., magnesium ion) to the sample. In some embodiments, the presence of an inhibitor in the sample prevents initiation of the sequencing reaction. In such embodiments, the reaction may be initiated by removal of the inhibitor, for example, by diluting out the inhibitor (e.g., via buffer exchange). Accordingly, it may be preferable that the sample is contacted with (e.g., loaded onto) the surface of the integrated device prior to initiation of the sequencing reaction.

In some embodiments, a sealant is added to the sample to overlay the initiated reaction. In some embodiments, the sealant is an oxygen-scavenging sealant. For example, following initiation of the reaction as shown in FIG. 6E, FIG. 6F depicts a layer 680 comprising an oxygen scavenging sealant 654 added to the sample. Properties, descriptions, and examples of suitable oxygen scavenging sealants are described herein.

Sample Preparation

In some aspects, the disclosure generally relates to improvements in the steps and processes between obtaining a sample for analysis and analyzing the sample. For example, in some embodiments, the disclosure relates to improvements in the steps and processes between obtaining a sample for sequencing and obtaining sequencing information from the sample. In some embodiments, the sample comprises a nucleic acid sample. In some aspects, preparing samples for sequencing generally involves making one or more physical and/or chemical modifications to a sample (e.g., a biological sample, a chemical sample, a nucleic acid sample, a protein sample) prior to subjecting the sample to sequencing analysis. In some embodiments, preparing a sample for sequencing involves generating a sequencing template.

As used herein, a "sequencing template" is a molecule that is the subject of an analysis (e.g., a sequencing analysis). In some embodiments, the sequencing template comprises a nucleic acid molecule. In some embodiments, the nucleic acid molecule is referred to as a "target" or "template" nucleic acid. In some embodiments, the nucleic acid molecule comprises at least one hybridized primer/polymerizing enzyme complex. For example, in some embodiments, the nucleic acid molecule is contacted with a sequencing primer that is complementary to a portion of the nucleic acid molecule such that the sequencing primer anneals to the nucleic acid molecule. This priming location generates a site in which a polymerizing enzyme (e.g., a DNA or RNA polymerase) may couple to the nucleic acid molecule to form a hybridized primer/polymerizing enzyme complex. Accordingly, in some embodiments, a sequencing template comprising at least one hybridized primer/polymerizing enzyme may be referred to as a "sequencing template complex."

The term "nucleic acid," as used herein, generally refers to a molecule comprising one or more nucleic acid subunits. A nucleic acid may include one or more subunits selected from adenine (A), cytosine (C), guanine (G), thymine (T), and uracil (U), or variants thereof. In some examples, a nucleic acid is deoxyribonucleic acid (DNA) or ribonucleic acid (RNA), or derivatives thereof. A nucleic acid may be single-stranded or double stranded. A nucleic acid may be circular. In some embodiments, a nucleic acid generally refers to any polymer of nucleotides.

The term "nucleotide," as used herein, generally refers to a nucleic acid subunit, which can include A, C, G, T, or U, or variants or analogs thereof. A nucleotide can include any subunit that can be incorporated into a growing nucleic acid strand. Such subunit can be an A, C, G, T, or U, or any other subunit that is specific to one or more complementary A, C, G, T, or U, or complementary to a purine (e.g., A or G, or variant or analogs thereof) or a pyrimidine (e.g., C, T, or U, or variant or analogs thereof). A subunit can enable individual nucleic acid bases or groups of bases (e.g., AA, TA, AT, GC, CG, CT, TC, GT, TG, AC, CA, or uracil-counterparts thereof) to be resolved. A nucleotide can comprises one or more phosphate groups. A nucleotide can comprise a methylated nucleobase. For example, a methylated nucleotide can be a nucleotide that comprises one or more methyl groups attached to the nucleobase (e.g., attached directly to a ring of the nucleobase, attached to a substituent of a ring of the nucleobase). Exemplary methylated nucleobases include 1-methylthymine, 1-methyluracil, 3-methyluracil, 3-methylcytosine, 5-methylcytosine, 1-methyladenine, 2-methyladenine, 7-methyladenine, N6-methyladenine, N6,N6-dimethyladenine, 1-methylguanine, 7-methylguanine, N2-methylguanine, and N2,N2-dimethylguanine.

The term "primer," as used herein, generally refers to a nucleic acid molecule (e.g., an oligonucleotide), which can include a sequence comprising A, C, G, T, and/or U, or variants or analogs thereof. A primer can be a synthetic oligonucleotide comprising DNA, RNA, PNA, or variants or analogs thereof. A primer can be designed such that its nucleotide sequence is complementary to a target or template nucleic acid, or the primer can comprise a random nucleotide sequence. In some embodiments, a primer can comprise a tail (e.g., a poly-A tail, an index adaptor, a molecular barcode, etc.). In some embodiments, a primer can comprise 5 to 15 bases, 10 to 20 bases, 15 to 25 bases, 20 to 30 bases, 25 to 35 bases, 30 to 40 bases, 35 to 45 bases, 40 to 50 bases, 45 to 55 bases, 50 to 60 bases, 55 to 65 bases, 60 to 70 bases, 65 to 75 bases, 70 to 80 bases, 75 to 85 bases, 80 to 90 bases, 85 to 95 bases, 90 to 100 bases, 95 to 105 bases, 100 to 150 bases, 125 to 175 bases, 150 to 200 bases, or more than 200 bases.

In some embodiments, a sample comprising a target nucleic acid may be extracted from a biological sample obtained from a subject (e.g., a human or other subject). In some embodiments, the subject may be a patient. In some embodiments, a target nucleic acid may be detected and/or sequenced for diagnostic, prognostic, and/or therapeutic purposes. In some embodiments, information for a sequencing assay may be useful to assist in the diagnosis, prognosis, and/or treatment of a disease or condition. In some embodiments, the subject may be suspected of having a health condition, such as a disease (e.g., cancer). In some embodiments, the subject may be undergoing treatment for a disease.

In some embodiments, a biological sample may be extracted from a bodily fluid or tissue of a subject, such as breath, saliva, urine, blood (e.g., whole blood or plasma), stool, or other bodily fluid or biopsy sample. In some examples, one or more nucleic acid molecules are extracted from the bodily fluid or tissue of the subject. The one or more nucleic acids may be extracted from one or more cells obtained from the subject, such as part of a tissue of the subject, or obtained from a cell-free bodily fluid of the subject, such as whole blood.

A biological sample may be processed in preparation for detection (e.g., sequencing). Such processing can include isolation and/or purification of the biomolecule (e.g., nucleic acid molecule) from the biological sample, and generation of more copies of the biomolecule. In some examples, one or more nucleic acid molecules are isolated and purified from a bodily fluid or tissue of the subject, and amplified through nucleic acid amplification, such as polymerase chain reaction (PCR). Then, the one or more nucleic acid molecules or subunits thereof can be identified, such as through sequencing. However, in some embodiments nucleic acid samples can be evaluated (e.g., sequenced) without requiring amplification.

As described in this application, sequencing can include the determination of individual subunits of a template biomolecule (e.g., nucleic acid molecule) by synthesizing another biomolecule that is complementary or analogous to the template, such as by synthesizing a nucleic acid molecule that is complementary to a template nucleic acid molecule and identifying the incorporation of nucleotides with time (e.g., sequencing by synthesis). As an alternative, sequencing can include the direct identification of individual subunits of the biomolecule.

During sequencing, signals indicative of individual subunits of a biomolecule may be collected in memory and processed in real time or at a later point in time to determine a sequence of the biomolecule. Such processing can include a comparison of the signals to reference signals that enable the identification of the individual subunits, which in some cases yields reads. Reads may be sequences of sufficient length (e.g., at least about 30, 50, 100 base pairs (bp) or more) that can be used to identify a larger sequence or region, e.g., that can be aligned to a location on a chromosome or genomic region or gene.

Sequence reads can be used to reconstruct a longer region of a genome of a subject (e.g., by alignment). Reads can be used to reconstruct chromosomal regions, whole chromosomes, or the whole genome. Sequence reads or a larger sequence generated from such reads can be used to analyze a genome of a subject, such as to identify variants or polymorphisms. Examples of variants include, but are not limited to, single nucleotide polymorphisms (SNPs) including tandem SNPs, small-scale multi-base deletions or insertions, also referred to as indels or deletion insertion polymorphisms (DIPs), Multi-Nucleotide Polymorphisms (MNPs), Short Tandem Repeats (STRs), deletions, including microdeletions, insertions, including microinsertions, structural variations, including duplications, inversions, translocations, multiplications, complex multi-site variants, copy number variations (CNV). Genomic sequences can comprise combinations of variants. For example, genomic sequences can encompass the combination of one or more SNPs and one or more CNVs.

The term "genome" generally refers to an entirety of an organism's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together constitutes the human genome. In some embodiments, the sequence of an entire genome is determined. However, in some embodiments, sequence information for a subset of a genome (e.g., one or a few chromosomes, or regions thereof) or for one or a few genes (or fragments thereof) is sufficient for diagnostic, prognostic, and/or therapeutic applications.

While some embodiments may be directed to diagnostic testing by detecting single molecules in a specimen, the inventors have also recognized that the methods and compositions of the present disclosure may be used to perform polypeptide (e.g., protein) sequencing or nucleic acid (e.g., DNA, RNA) sequencing of one or more nucleic acid segments of, for example, genes.

Sequencing

In some embodiments, aspects of the present application can be used in methods related to assays of biological samples. In exemplary embodiments, methods provided herein are useful in techniques used to determine the sequence of one or more nucleic acids or polypeptides in the sample and/or to determine the presence or absence of one or more nucleic acid or polypeptide variants (e.g., one or more mutations in a gene of interest) in the sample. In some embodiments, tests can be performed on patient samples (e.g., human patient samples) to provide nucleic acid sequence information or to determine the presence or absence of one or more nucleic acids of interest for diagnostic, prognostic, and/or therapeutic purposes. In some examples, diagnostic tests can include sequencing a nucleic acid molecule in a biological sample of a subject, for example by sequencing cell free DNA molecules and/or expression products (e.g., RNA) in a biological sample of the subject. For example, the present disclosure provides methods and compositions that may be advantageously utilized in the technologies described in co-pending U.S. patent application Ser. Nos. 14/543,865, 14/543,867, 14/543,888, 14/821,656, 14/821,686, 14/821,688, 15/161,067, 15/161,088, 15/161,125, 15/255,245, 15/255,303, 15/255,624, 15/261,697, 15/261,724, 62/289,019, 62/296,546, 62/310,398, 62/339,790, 62/343,997, 62/344,123, and 62/426,144, the contents of each of which are incorporated herein by reference.

Some aspects of the application are useful in techniques capable of sequencing biological polymers, such as nucleic acids and proteins. In some embodiments, methods and compositions described in the application can be used in techniques that identify a series of nucleotide or amino acid monomers that are incorporated into a nucleic acid or protein (e.g., by detecting a time-course of incorporation of a series of labeled nucleotide or amino acid monomers). In some embodiments, methods and compositions described in the application can be incorporated into techniques that identify a series of nucleotides that are incorporated into a template-dependent nucleic acid sequencing reaction product synthesized by a polymerizing enzyme.

During sequencing, a polymerizing enzyme may couple (e.g., attach) to a priming location of a target nucleic acid molecule (e.g., a nucleic acid molecule of a sequencing template). The priming location can comprise a primer that is complementary to a portion of the target nucleic acid molecule. As an alternative the priming location is a gap or nick that is provided within a double stranded segment of the target nucleic acid molecule. A gap or nick can be from 0 to at least 1, 2, 3, 4, 5, 6, 7, 8, 9, 10, 20, 30, or 40 nucleotides in length. A nick can provide a break in one strand of a double stranded sequence, which can provide a priming location for a polymerizing enzyme, such as, for example, a strand displacing polymerase enzyme.

In some cases, a sequencing primer can be annealed to a target nucleic acid molecule that may or may not be immobilized to a solid support. A solid support can comprise, for example, a sample well on an integrated device used for nucleic acid sequencing. In some embodiments, a sequencing primer may be immobilized to a solid support and hybridization of the target nucleic acid molecule also immobilizes the target nucleic acid molecule to the solid support. In some embodiments, a polymerase is immobilized to a solid support and soluble primer and target nucleic acid are contacted to the polymerase. However, in some embodiments a complex comprising a polymerase, a target nucleic acid and a primer is formed in solution and the complex is immobilized to a solid support (e.g., via immobilization of the polymerase, primer, and/or target nucleic acid). In some embodiments, none of the components in a sample well are immobilized to a solid support. For example, in some embodiments, a complex comprising a polymerase, a target nucleic acid, and a primer is formed in solution and the complex is not immobilized to a solid support.

Under appropriate conditions, a polymerase enzyme that is contacted to an annealed primer/target nucleic acid can add or incorporate one or more nucleotides onto the primer, and nucleotides can be added to the primer in a 5' to 3', template-dependent fashion. Such incorporation of nucleotides onto a primer (e.g., via the action of a polymerase) can generally be referred to as a primer extension reaction. Each nucleotide can be associated with a detectable tag that can be detected and identified (e.g., based on its luminescent lifetime and/or other characteristics) during the nucleic acid extension reaction and used to determine each nucleotide incorporated into the extended primer and, thus, a sequence of the newly synthesized nucleic acid molecule. Via sequence complementarity of the newly synthesized nucleic acid molecule, the sequence of the target nucleic acid molecule can also be determined. In some cases, annealing of a sequencing primer to a target nucleic acid molecule and incorporation of nucleotides to the sequencing primer can occur at similar reaction conditions (e.g., the same or similar reaction temperature) or at differing reaction conditions (e.g., different reaction temperatures). In some embodiments, sequencing by synthesis methods can include the presence of a population of target nucleic acid molecules (e.g., copies of a target nucleic acid) and/or a step of amplification of the target nucleic acid to achieve a population of target nucleic acids. However, in some embodiments, sequencing by synthesis is used to determine the sequence of a single molecule in each reaction that is being evaluated (and nucleic acid amplification is not required to prepare the target template for sequencing). In some embodiments, a plurality of single molecule sequencing reactions are performed in parallel (e.g., on a single integrated device) according to aspects of the present application. For example, in some embodiments, a plurality of single molecule sequencing reactions are each performed in separate reaction chambers on an integrated device.

Embodiments are capable of loading sequencing templates comprising nucleic acid molecules having lengths greater than or equal to about 10 base pairs (bp), 50 bp, 100 bp, 200 bp, 300 bp, 400 bp, 500 bp, 1000 bp, 10,000 bp, 20,000 bp, 30,000 bp, 40,000 bp, 50,000 bp, or 100,000 bp. In some embodiments, the target nucleic acid molecule used in single molecule sequencing is a single stranded target nucleic acid template that is added or immobilized to a sample well containing at least one additional component of a sequencing reaction (e.g., a polymerizing enzyme, such as a DNA polymerase, and a sequencing primer) immobilized or attached to a solid support such as the bottom or side walls of the sample well. The target nucleic acid molecule or the polymerase can be attached to a sample wall, such as at the bottom surface or side walls of the sample well directly or through a linker. The sample well also can contain any other reagents needed for nucleic acid synthesis via a primer extension reaction, such as, for example suitable buffers, co-factors, enzymes (e.g., a polymerase) and deoxyribonucleoside polyphosphates, such as, e.g., deoxyribonucleoside triphosphates, including deoxyadenosine triphosphate (dATP), deoxycytidine triphosphate (dCTP), deoxyguanosine triphosphate (dGTP), deoxyuridine triphosphate (dUTP) and deoxythymidine triphosphate (dTTP) dNTPs, that may optionally comprise detectable moieties (e.g., luminescent tags).

In some embodiments, the single-stranded target nucleic acid template can be contacted with a sequencing primer, dNTPs, polymerase, and other reagents necessary for nucleic acid synthesis. In some embodiments, all appropriate dNTPs can be contacted with the single-stranded target nucleic acid template simultaneously (e.g., all dNTPs are simultaneously present) such that incorporation of dNTPs can occur continuously. In other embodiments, the dNTPs can be contacted with the single-stranded target nucleic acid template sequentially, where the single-stranded target nucleic acid template is contacted with each appropriate dNTP separately, with washing steps in between contact of the single-stranded target nucleic acid template with differing dNTPs. Such a cycle of contacting the single-stranded target nucleic acid template with each dNTP separately followed by washing can be repeated for each successive base position of the single-stranded target nucleic acid template to be identified. In some embodiments, the sequencing primer anneals to the single-stranded target nucleic acid template and the polymerase consecutively incorporates the dNTPs (or other deoxyribonucleoside polyphosphate) to the primer based on the single-stranded target nucleic acid template.

Polymerases

The terms "polymerase" and "polymerizing enzyme," as used herein, generally refer to any enzyme capable of catalyzing a polymerization reaction. Examples of polymerases include, without limitation, a nucleic acid polymerase, a transcriptase or a ligase. A polymerase can be a polymerization enzyme.

Embodiments directed towards single molecule nucleic acid extension (e.g., for nucleic acid sequencing) may use any polymerase that is capable of synthesizing a nucleic acid complementary to a target nucleic acid molecule. In some embodiments, a polymerase may be a DNA polymerase, an RNA polymerase, a reverse transcriptase, and/or a mutant or altered form of one or more thereof.

Examples of polymerases include, but are not limited to, a DNA polymerase, an RNA polymerase, a thermostable polymerase, a wild-type polymerase, a modified polymerase, E. coli DNA polymerase I, T7 DNA polymerase, bacteriophage T4 DNA polymerase φ29 (phi29) DNA polymerase, Taq polymerase, Tth polymerase, Tli polymerase, Pfu polymerase, Pwo polymerase, Vent® polymerase, Deep Vent™ polymerase, Ex Taq™ polymerase, LA Taq™ polymerase, Sso polymerase, Poc polymerase, Pab polymerase, Mth polymerase, ES4 polymerase, Tru polymerase, Tac polymerase, Tne polymerase, Tma polymerase, Tea polymerase, Tih polymerase, Tfi polymerase, Platinum® Taq polymerases, Tbr polymerase, Tfl polymerase, Tth polymerase, Pfuturbo® polymerase, Pyrobest™ polymerase, Pwo polymerase, KOD polymerase, Bst polymerase, Sac polymerase, Klenow fragment, polymerase with 3' to 5' exonuclease activity, and variants, modified products and derivatives thereof. In some embodiments, the polymerase is a single subunit polymerase. Additional example of polymerases include M2Y polymerase, *Lucilia cuprina* polymerase, *Enterococcus faecium* polymerase, *Bacillus* phage VMY22 polymerase, *Bacillus* phage GA-1 polymerase, *Actinomyces* phage AV-1 polymerase, Candidatus Moranbacteria polymerase, *Bacillus* phage MG-B1 polymerase, *Eggerthella* sp. polymerase, *Streptococcus* phage CP-7 polymerase, *Bacteroides* sp. polymerase, and *Chlamydia trachomatis* polymerase. Non-limiting examples of DNA polymerases and their properties are described in detail in, among other places, DNA Replication 2nd edition, Kornberg and Baker, W. H. Freeman, New York, N.Y. (1991).

Upon base pairing between a nucleobase of a target nucleic acid and the complementary dNTP, the polymerase incorporates the dNTP into the newly synthesized nucleic acid strand by forming a phosphodiester bond between the 3' hydroxyl end of the newly synthesized strand and the alpha phosphate of the dNTP. In some embodiments, the polymerase is a polymerase with high processivity. However, in some embodiments, the polymerase is a polymerase with reduced processivity. Polymerase processivity generally refers to the capability of a polymerase to consecutively incorporate dNTPs into a nucleic acid template without releasing the nucleic acid template.

In some embodiments, the polymerase is a polymerase with low 5'-3' exonuclease activity and/or 3'-5' exonuclease. In some embodiments, the polymerase is modified (e.g., by amino acid substitution) to have reduced 5'-3' exonuclease activity and/or 3'-5' activity relative to a corresponding wild-type polymerase. Further non-limiting examples of DNA polymerases include 9° Nm™ DNA polymerase (New England Biolabs), and a P680G mutant of the Klenow exo-polymerase (Tuske et al. (2000) JBC 275(31):23759-23768). In some embodiments, a polymerase having reduced processivity provides increased accuracy for sequencing templates containing one or more stretches of nucleotide repeats (e.g., two or more sequential bases of the same type).

Embodiments directed toward single molecule RNA extension (e.g., for RNA sequencing) may use any reverse transcriptase that is capable of synthesizing complementary DNA (cDNA) from an RNA template. In such embodiments, a reverse transcriptase can function in a manner similar to polymerase in that cDNA can be synthesized from an RNA template via the incorporation of dNTPs to a reverse transcription primer annealed to an RNA template. The cDNA can then participate in a sequencing reaction and its sequence determined. The determined sequence of the cDNA can then be used, via sequence complementarity, to determine the sequence of the original RNA template. Examples of reverse transcriptases include Moloney Murine Leukemia Virus reverse transcriptase (M-MLV), avian myeloblastosis virus (AMV) reverse transcriptase, human immunodeficiency virus reverse transcriptase (HIV-1) and telomerase reverse transcriptase.

The processivity, exonuclease activity, relative affinity for different types of nucleic acid, or other property of a nucleic acid polymerase can be increased or decreased by one of skill in the art by mutation or other modification relative to a corresponding wild-type polymerase. In some embodiments, a sample comprising a polymerase may be loaded into a sample well by contacting the sample with the surface of an integrated device, as described herein.

Sample Wells

In some aspects, the disclosure provides methods of loading a sample into a sample well comprised by an integrated device. As used herein, an "integrated device" is a device capable of interfacing with a base instrument. In some embodiments, an integrated device may comprise one or more sample wells and/or sensors. In some embodiments, an integrated device may be capable of interfacing with a base instrument that emits or detects light. In such embodiments, the integrated device may comprise one or more sample wells, each of which includes a waveguide.

An integrated device of the type described herein may comprise one or more sample wells configured to receive molecules of interest therein. In some embodiments, a sample well receives a molecule of interest that may be disposed on a surface of the sample well, such as a bottom surface. In some embodiments, a sample well is formed within an integrated device, wherein the bottom surface of the sample well is distal to the surface of the integrated device into which it is formed. In some embodiments, the bottom surface on which the molecule of interest is to be disposed may have a distance from a waveguide that is configured to excite the molecule of interest with a desired level of excitation energy. In some embodiments, the sample well may be positioned, with respect to a waveguide, such that an evanescent field of an optical mode propagating along the waveguide overlaps with the molecule of interest.

A sample well may have a top opening at the surface of an integrated device through which a molecule of interest may be placed in the sample well. The size of the top opening may depend on different factors, such as the size of the molecules of interest (e.g., sequencing templates) in the sample being loaded. In some embodiments, the size of the top opening may depend upon the instrument or apparatus in which integrated device comprising the sample well is being utilized. For example, in devices that detect light from within the sample well, background signals may result from stray light. When a molecule of interest is disposed in the sample well and excited with excitation energy, background signals may cause undesired fluctuations in the emission energy, thus making the measurement noisy. To limit such fluctuations, the size of the top opening may be configured to block at least a portion of the background signals.

The volume of a sample well may be between about $10^{-21}$ liters and about $10^{-15}$ liters, in some implementations. Because the sample well has a small volume, detection of single-sample events (e.g., single-molecule events) may be possible even though molecules of interest may be concentrated in an examined specimen at concentrations that are similar to those found in natural environments. For example, micromolar concentrations of the molecule of interest may be present in a specimen that is placed in contact with the integrated device, but at the pixel level only about one molecule of interest (or single molecule event) may be within a sample well at any given time.

Statistically, some sample wells may contain no molecules of interest and some may contain more than one molecule of interest. However, an appreciable number of sample wells may contain a single molecule of interest (e.g., at least 30% in some embodiments), so that single-molecule analysis can be carried out in parallel for a large number of sample wells. Because single-molecule or single-sample events may be analyzed at each sample well, the integrated device makes it possible to detect individual events that may otherwise go unnoticed in ensemble averages.

Sample Well Functionalization

In certain embodiments, techniques described herein relate to the loading of a molecule into a sample well, where the molecule is confined in a target volume of the sample well (e.g., a reaction volume). In some embodiments, the target volume is a region within a sample well. In certain embodiments, the sample well comprises a bottom surface comprising a first material and sidewalls formed by a plurality of metal or metal oxide layers. In some embodiments, the first material is a transparent material or glass. In some embodiments, the bottom surface is flat. In some embodiments, the bottom surface is a curved well. In some embodiments, the bottom surface includes a portion of the sidewalls below the sidewalls formed by a plurality of metal or metal oxide layers. In some embodiments, the first material is fused silica or silicon dioxide. In some embodiments, the plurality of layers each comprise a metal (e.g., Al, Ti) or metal oxide (e.g., $Al_2O_3$, $TiO_2$, TiN).

In embodiments when one or more molecule or complex (e.g., a sequencing template) is immobilized on the bottom surface, it may be desirable to functionalize the bottom surface to allow for attachment of one or more molecules or complexes. In certain embodiments, the bottom surface comprises a transparent glass. In certain embodiments, the bottom surface comprises fused silica or silicon dioxide. In some embodiments, the bottom surface is functionalized with a silane. In some embodiments, the bottom surface is functionalized with an ionically charged polymer. In some embodiments, the ionically charged polymer comprises poly(lysine). In some embodiments, the bottom surface is functionalized with poly(lysine)-graft-poly(ethylene glycol). In some embodiments, the bottom surface is functionalized with biotinylated bovine serum albumin (BSA).

In certain embodiments, the bottom surface is functionalized with a coating comprising nitrodopa groups. In certain embodiments, the coating comprises groups of formula:

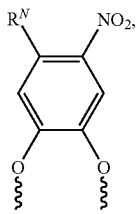

wherein $R^N$ is an optionally substituted alkyl chain and ⁓ is hydrogen or a point of attachment to the surface. In some embodiments, $R^N$ comprises a polymer. In some embodiments, $R^N$ comprises a poly(lysine) or a poly(ethylene glycol). In some embodiments, $R^N$ comprises a biotinylated poly(ethylene glycol). In some embodiments, the coating comprises a co-polymer of poly(lysine) comprising lysine monomers, wherein the lysine monomers independently comprise PEG, biotinylated PEG, nitrodopa groups, phosphonate groups, or silanes. In certain embodiments, the coating comprises a polymer of formula (P):

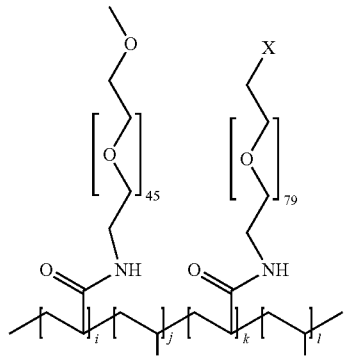

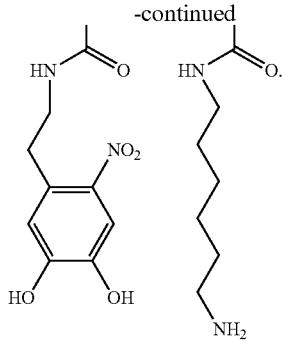

In some embodiments, X is —OMe, a biotin group, phosphonate, or silane. In some embodiments, each of i, j, k, and l is independently an integer between 0 and 100, inclusive.

In some embodiments, the bottom surface is functionalized with a silane comprising an alkyl chain. In some embodiments, the bottom surface is functionalized with a silane comprising an optionally substituted alkyl chain. In some embodiments, the bottom surface is functionalized with a silane comprising a poly(ethylene glycol) chain. In some embodiments, the bottom surface is functionalized with a silane comprising a coupling group. For example the coupling group may comprise chemical moieties, such as amine groups, carboxyl groups, hydroxyl groups, sulfhydryl groups, metals, chelators, and the like. Alternatively, they may include specific binding elements, such as biotin, avidin, streptavidin, neutravidin, lectins, SNAP-tags™ or substrates therefore, associative or binding peptides or proteins, antibodies or antibody fragments, nucleic acids or nucleic acid analogs, or the like. Additionally, or alternatively, the coupling group may be used to couple an additional group that is used to couple or bind with the molecule of interest, which may, in some cases include both chemical functional groups and specific binding elements. By way of example, a coupling group, e.g., biotin, may be deposited upon a substrate surface and selectively activated in a given area. An intermediate binding agent, e.g., streptavidin, may then be coupled to the first coupling group. The molecule of interest, which in this particular example would be biotinylated, is then coupled to the streptavidin.

In some embodiments, the bottom surface is functionalized with a silane comprising biotin, or an analog thereof. In some embodiments, the bottom surface is functionalized with a silane comprising a poly(ethylene) glycol chain, wherein the poly(ethylene glycol) chain comprises biotin. In certain embodiments, the bottom surface is functionalized with a mixture of silanes, wherein at least one type of silane comprises biotin and at least one type of silane does not comprise biotin. In some embodiments, the mixture comprises about 10 fold less, about 25 fold less, about 50 fold less, about 100 fold less, about 250 fold less, about 500 fold less, or about 1000 fold less of the biotinylated silane than the silane not comprising biotin.

The polymerase complex may be immobilized on the bottom surface by exposing the complex to the functionalized surface in a binding mixture. In some embodiments, the binding mixture comprises one or more salts. In some embodiments, a salt comprises potassium acetate. In some embodiments, a salt comprises calcium chloride. In some embodiments, a salt is present in a concentration of between about 1 mM and about 10 mM. In some embodiments, a salt is present in a concentration of between about 10 mM and about 50 mM. In some embodiments, a salt is present in a concentration of between about 50 mM and about 100 mM. In some embodiments, a salt is present in a concentration of between about 100 mM and about 250 mM. In some embodiments, the concentration of potassium acetate is about 75 mM. In some embodiments, the concentration of calcium chloride is about 10 mM. In some embodiments, the binding mixture comprises a reducing agent. In some embodiments, a reducing agent comprises dithiothreitol (DTT). In some embodiments, the reducing agent is present in a concentration of between about 1 mM and about 20 mM. In some embodiments, the concentration of dithiothreitol is about 5 mM. In some embodiments, the binding mixture comprises a buffer. In some embodiments, a buffer comprises MOPS. In some embodiments, a buffer is present in a concentration of between about 10 mM and about 100 mM. In some embodiments, the concentration of MOPS is about 50 mM. In some embodiments, a buffer is present at a pH of between about 5.5 and about 6.5. In some embodiments, a buffer is present at a pH of between about 6.5 and about 7.5 In some embodiments, a buffer is present at a pH of between about 7.5 and about 8.5 In some embodiments, the binding mixture comprises deoxynucleotide triphosphates (dNTPs). In some embodiments, the deoxynucleotide triphosphates are present in a concentration of between 250 nM and 10 µM. In some embodiments, the concentration of dNTPs is about 2 µM. In some embodiments, the binding mixture comprises a surfactant. In some embodiments, the surfactant is a Tween surfactant (e.g., Tween 20). In some embodiments, the surfactant is present in a volume percent of between about 0.01% and about 0.1%. In some embodiments, the volume percent of Tween is about 0.03%.

EXAMPLES

Example 1: Methylcellulose Sample Loading

A 2% by weight METHOCEL solution was made up in deionized water following a standard dissolution protocol (methyl cellulose, Sigma M0387, ~1,500 mPa·s at 2% and 20° C., ~63,000 Da). For use during loading of sequencing template complex (polymerase/primer/template complex), the 2% METHOCEL solution was mixed 9:1 with a 10× solution of Binding Buffer (500 mM MOPS pH 7.5, 750 mM potassium acetate, 100 mM DTT, 20 mM calcium acetate, 20 µM NTPs (each), 0.1% w/w tween 20). The resultant 1.8% polymer solution in buffer contains the same ionic composition as a sequencing template complex loading solution in 1× Binding Buffer (50 mM MOPS pH 7.5, 75 mM potassium acetate, 10 mM DTT, 2 mM calcium acetate, 2 µM NTPs (each), 0.01% w/w tween 20).

A solution of tween 20 (0.1%) was added to a sequencing chip (e.g., an integrated device) having sample wells of 270 nm in depth and allowed to incubate for 10 minutes. Upon removal of tween 20, the sequencing chip was washed once with 1× Binding Buffer before the addition of 30 µL Binding Buffer to the integrated device. A solution containing sequencing template complex was added to the integrated device to a final concentration of 250-1000 pM and mixed well. The mixed solution was overlaid with a solution of 1.8% methylcellulose in Binding Buffer. The sequencing chip was subsequently incubated for 30-60 minutes at room temperature. This incubation period presumably allows the polymerase-streptavidin fusion of a sequencing template complex to become immobilized in a sample well on the sequencing chip, the sample wells having been coated with biotin.

Following the incubation period, the solution was removed from the sequencing chip. The sequencing chip was washed three times with Binding Buffer before washing once with Reaction Buffer (65 mM MOPS pH 7.7, 120 mM potassium acetate, 20 mM magnesium acetate, 10 mM DTT, 8 mM protocatechuic acid, 6 mM 4-nitrobenzyl alcohol, 1× protocatechuate 3,4-dioxygenase). Finally, a volume of Reaction Buffer was added to the sequencing chip and covered with an equal volume of mineral oil. The sequencing reaction was monitored in real-time using methods described in pending U.S. application Ser. Nos. 14/821,656, 15/261,697, 15/261,724 and 15/161,125. A representative sequencing reaction is depicted by the intensity and time traces shown in FIG. 7A. In this reaction, a 9.1 kb double-stranded DNA template was sequenced across a read length of over 1.2 kb (FIG. 7B).

To assess the effects of methylcellulose on the loading of large templates, two sequencing chips were each loaded with the same 9.1 kb template DNA, one using an overlay of 2% methylcellulose (as described above) and one with no overlay. Both chips were loaded at 660 pM template for 1 hour. Multiple incorporation traces were detected from the methylcellulose-loaded chip, while no sequencing activity was detected on the integrated device without overlay. SYBR Gold, a fluorescent DNA-binding dye, was then added to each of the sequencing chips. Imaging results are depicted in FIG. 8, which illustrates the dramatic difference in DNA staining. Approximately 30% of the sample wells on the methylcellulose-loaded chip were brightly stained, indicating the presence of DNA template, whereas no staining was observed on the integrated device without methylcellulose overlay.

In a similar experiment, two further sequencing chips were each loaded with the same 5.4 kb template DNA, one using an overlay of 2.7% methylcellulose and one loaded by diffusion alone. Both chips were loaded with 2.5 nM DNA template for 1.5 hours. SYBR Gold was then added to each of the sequencing chips. Imaging results are depicted in FIG. 9, which illustrates the dramatic difference in DNA staining. Approximately 25 sample wells were loaded with single templates in the methylcellulose chip compared to approximately 13 sample wells loaded by diffusion alone.

Example 2: Solid State Crowding Agent

FIG. 10 depicts an experimental setup that was used to evaluate the potential of agarose as a solid state crowding agent. As shown, the ~4 mm portion above the nut of a screw represents a body that can be inserted into a bulk sample well of an integrated device (e.g., an array, for example in a depressed region, or other vessel that holds the bulk volume of a loaded sample). Three conditions are depicted to illustrate the process whereby the agarose acts as a crowding agent. The "No Agarose" screw is a body without any crowding agent. The "Dried Agarose" screw shows a body that is coated with dried agarose. As can be seen in FIG. 10, the dried agarose approximately fills in the threading of the screw. The "Hydrated Agarose" screw represents a dried agarose body following insertion into the bulk sample well of an integrated device that has been loaded with a sample. The swelling of the agarose coating on the body indicates rehydration of the agarose by water in the bulk sample well, the effect of which would produce an increased concentration of sequencing template in bulk solution.

EQUIVALENTS AND SCOPE

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents, and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B," the disclosure also contemplates the alternative embodiments "a composition consisting of A and B" and "a composition consisting essentially of A and B."

What is claimed is:

1. A method of loading a molecule of interest into a sample well, the method comprising:
    contacting a sample comprising a molecule of interest to a surface of a substrate, wherein the molecule of interest comprises a sequencing template, and wherein the surface of the substrate comprises a plurality of sample wells; and
    adding a layer of a composition comprising a crowding agent over the sample on the surface of the substrate, wherein the crowding agent excludes the molecule of interest from the layer relative to other components in the sample, wherein each sample well has a volume of about $10^{-21}$ liters and about $10^{-15}$ liters, and wherein the concentration of the crowding agent in the composition is between about 0.1% by weight to about 20% by weight.

2. The method of claim 1, wherein the sequencing template comprises a nucleic acid molecule having at least one hybridized primer/polymerizing enzyme complex.

3. The method of claim 1, wherein the crowding agent is a polysaccharide, optionally wherein the polysaccharide is a cellulose compound.

4. The method of claim 3, wherein the cellulose compound is selected from the group consisting of methyl cellulose, ethyl cellulose, ethyl methyl cellulose, hydroxyethyl cellulose, hydroxypropyl cellulose, hydroxyethyl methyl cellulose, hydroxypropyl methyl cellulose, ethyl hydroxyethyl cellulose, and carboxymethyl cellulose.

5. The method of claim 1, wherein the crowding agent is a polyether compound.

6. The method of claim 5, wherein the polyether compound is selected from the group consisting of polyethylene glycol, polypropylene glycol, paraformaldehyde, polytetramethylene glycol, and polyphenyl ether.

7. The method of claim 1, wherein the crowding agent is a polyamide compound.

8. The method of claim 7, wherein the polyamide compound is selected from the group consisting of linear polyvinylpyrrolidone and cyclic polyvinylpyrrolidone.

9. The method of claim 1, wherein the composition comprising the crowding agent is provided as a film, optionally wherein the film is a material selected from a crosslinked gel or a dehydrated solution.

10. The method of claim 1, wherein the composition comprising the crowding agent is provided as a solution.

11. The method of claim 10, wherein the concentration of the crowding agent in the solution is about 0.6% by weight, about 0.9% by weight, about 2.0% by weight, or about 2.3% by weight.

12. The method of claim 10, wherein the concentration of the crowding agent in the solution is between about 0.1% by weight to about 1.0% by weight, between about 1.0% by weight to about 2.0% by weight, between about 2.0% by weight to about 3.0% by weight, between about 3.0% by weight to about 4.0% by weight, or between about 4.0% by weight to about 5.0% by weight.

13. The method of claim 1 further comprising contacting the sample with a condensing agent configured to reduce the pervaded volume of the molecule of interest.

14. The method of claim 13, wherein the condensing agent comprises a polycation that is polycationic in the sample.

15. The method of claim 14, wherein the polycation is selected from spermine, spermidine, polylysine, polyarginine, polyhistidine, polyornithine, putrescine, and protamine.

16. The method of claim 1, wherein each sample well of the plurality of sample wells comprises a bottom surface distal to the surface of the substrate, and wherein the bottom surface comprises at least one coupling group configured to bind the molecule of interest.

17. The method of claim 1, further comprising contacting the sample with a sealant, optionally wherein the sealant comprises an oxygen scavenging sealant that comprises an oxidizable agent and a catalyst.

18. The method of claim 17, wherein the oxidizable agent is an organic compound comprising at least one ethylenic bond, and the catalyst comprises a transition metal and a counterion.

19. The method of claim 1, further comprising subjecting the sample to a next generation sequencing technique.

* * * * *